(12) United States Patent
Fisker et al.

(10) Patent No.: US 9,308,055 B2
(45) Date of Patent: Apr. 12, 2016

(54) DESIGNING A DENTAL POSITIONING JIG

(71) Applicant: 3SHAPE A/S, Copenhagen K (DK)

(72) Inventors: Rune Fisker, Virum (DK); Tais Clausen, Klagshamn (SE)

(73) Assignee: 3SHAPE A/S, Copenhagen (DK)

( * ) Notice: Subject to any disclaimer, the term of this patent is extended or adjusted under 35 U.S.C. 154(b) by 0 days.

(21) Appl. No.: 14/416,990

(22) PCT Filed: Jul. 25, 2013

(86) PCT No.: PCT/EP2013/065714
§ 371 (c)(1),
(2) Date: Jan. 23, 2015

(87) PCT Pub. No.: WO2014/016378
PCT Pub. Date: Jan. 30, 2014

(65) Prior Publication Data
US 2015/0202024 A1    Jul. 23, 2015

Related U.S. Application Data

(60) Provisional application No. 61/676,044, filed on Jul. 26, 2012.

(30) Foreign Application Priority Data

Jul. 25, 2012   (DK) ................................. 2012 70451

(51) Int. Cl.
*A61C 8/00* (2006.01)
*A61C 1/08* (2006.01)
(Continued)

(52) U.S. Cl.
CPC ................ *A61C 1/084* (2013.01); *A61C 8/008* (2013.01); *A61C 8/0089* (2013.01);
(Continued)

(58) Field of Classification Search
CPC .. A61C 8/008; A61C 8/0089; A61C 13/0004; A61C 13/0013; A61C 13/0019; A61C 13/34
See application file for complete search history.

(56) References Cited

U.S. PATENT DOCUMENTS 6,319,006 B1    11/2001   Scherer et al.
2004/0219480 A1 11/2004   Malin
(Continued)

FOREIGN PATENT DOCUMENTS

EP    1 486 900 A1    12/2004
JP    07-95989 A       4/1995
(Continued)

OTHER PUBLICATIONS

International Search Report (PCT/ISA/210) mailed on Sep. 18, 2013, by the European Patent Office as the International Searching Authority for International Application No. PCT/EP2013/065714.
(Continued)

*Primary Examiner* — Ralph Lewis
(74) *Attorney, Agent, or Firm* — Buchanan Ingersoll & Rooney PC

(57) ABSTRACT

A method, a system, and a user interface for creating a virtual positioning jig for manufacturing a positioning jig, where the manufactured positioning jig is for use in positioning a manufactured dental restoration at a patient's set of teeth, the method including: obtaining a digital 3D representation of the set of teeth; designing a virtual model of the dental restoration at the digital 3D representation; creating an inner surface and an outer surface of the virtual positioning jig; and defining a through hole of the virtual positioning jig at the implant region.

21 Claims, 12 Drawing Sheets

(51) Int. Cl.
*A61C 13/00* (2006.01)
*A61C 13/34* (2006.01)
*G06F 17/50* (2006.01)

(52) U.S. Cl.
CPC ........ *A61C 13/0004* (2013.01); *A61C 13/0013* (2013.01); *A61C 13/0019* (2013.01); *A61C 13/34* (2013.01); *G06F 17/50* (2013.01)

(56) References Cited

U.S. PATENT DOCUMENTS

| | | |
|---|---|---|
| 2008/0085489 A1 | 4/2008 | Schmitt |
| 2008/0153067 A1 | 6/2008 | Berckmans et al. |
| 2011/0066267 A1 | 3/2011 | Schmitt |
| 2012/0046668 A1 | 2/2012 | Gantes |
| 2012/0143364 A1 | 6/2012 | Mcleod |

FOREIGN PATENT DOCUMENTS

| | | |
|---|---|---|
| WO | WO 2008043056 A2 | 4/2008 |
| WO | 2008/112784 A2 | 9/2008 |
| WO | WO 2013/092744 A1 | 6/2013 |

OTHER PUBLICATIONS

Written Opinion (PCT/ISA/237) issued on Sep. 18, 2013, by European Patent Office as the International Searching Authority for International Application No. PCT/EP2013/065714.

English Translation of Danish Office Action issued on Mar. 7, 2013, by the Danish Patent Office in corresponding Danish Patent Application No. PA 2012 70451. (4 pages).

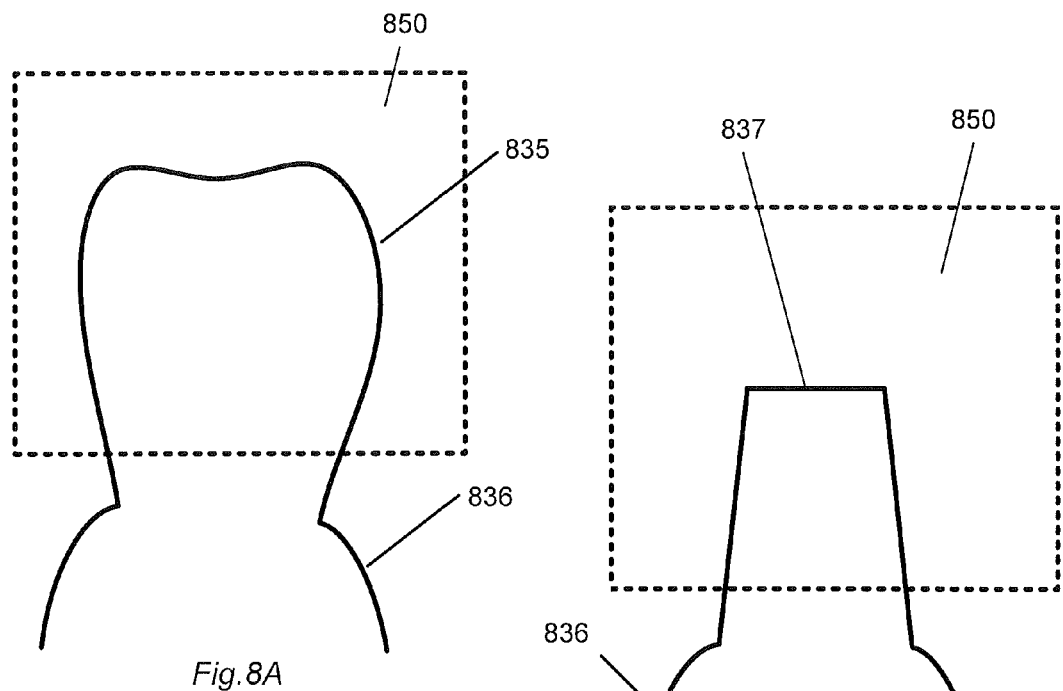
Fig.8A
Fig.8B
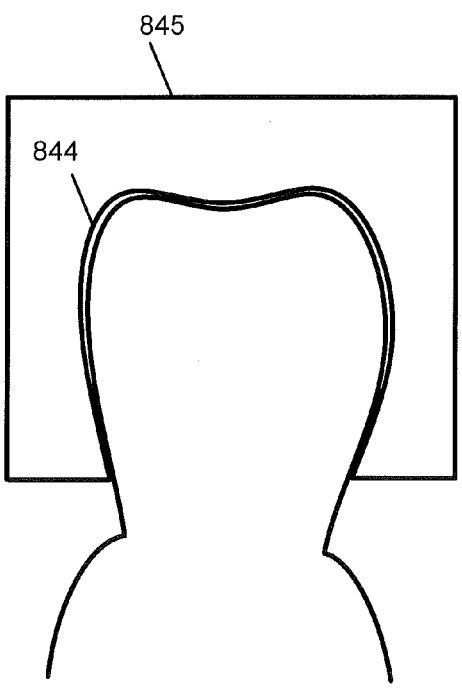
Fig.8C
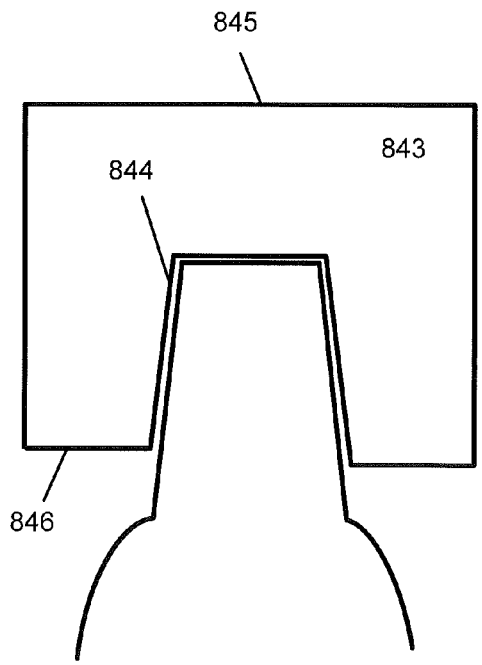
Fig.8D

DESIGNING A DENTAL POSITIONING JIG

FIELD OF THE INVENTION

This invention generally relates to a method for creating a virtual positioning jig for manufacturing a positioning jig, where said manufactured positioning jig is for use when positioning a manufactured dental restoration at an implant region of a patient's set of teeth. More particularly, the invention relates to a method wherein a through hole of the positioning jig is defined in the virtual positioning jig, where the through hole in the manufactured positioning jig is located at the implant region thus allowing a dentist to access this region through the positioning jig.

BACKGROUND OF THE INVENTION

Dental prosthetic procedures for replacing one or more teeth with dental restorations, such as crowns and bridges, are performed on a daily basis by dentists worldwide. In cases where a patient's original tooth is either missing or is ill or damaged to an extent where it no longer can serve as the support for a dental restoration, the dentist may decide to place an implant in the patient's jaw bone, such that the dental restoration can be supported by this implant e.g. via an implant abutment. When arranged in the patient's mouth implants can replace the parts of the teeth which are not visible in a 3D surface scan, such as the roots of the tooth. If the original tooth or any remains of it still are present in the patient's mouth these are extracted and a bore for the implant is surgically drilled into the jaw bone. The implant is placed in this bore and the surrounding bone grows into very close apposition to the implant such that the implant is secured to the bone. This process is also known as osseointegration. In particular titanium has shown to have very good osseointegration properties and is currently the most preferred material to use for implants.

Osseointegration usually takes several months to complete and during that period of time a healing abutment can be placed at the implant in order to e.g. ensure that the implant is kept free of dirt and food. The healing abutment can further be used for shaping the soft tissue in the region where the original tooth was extracted from such that the soft tissue maintains an anatomically correct shape instead of collapsing into the space which previously was occupied by the extracted tooth.

Once the osseointegration is completed and the implant is secured in the bone such that it can be used as support for dental restorations, the healing abutment is removed and the final dental restoration is arranged in the implant. This is often an implant abutment placed in the implant to serve as an interface between the implant and an anatomical layer, such as a crown or a bridge, and coping layers. The implant abutment can be secured in the implant using a retention screw and the anatomical layer can be cemented to the implant abutment.

Several implants are provided with an internal anti-rotational feature which can be engaged by a corresponding feature of a so-called engaging abutment such that rotation of the abutment around the longitudinal axis of the implant is prevented when the abutment is arranged at the implant, such that the orientation of the abutment is fixed. For some applications, such as for multiple implant restoration units where some rotational freedom is advantageous, non-engaging abutments may be preferred. The correct arrangement of especially non-engaging abutments, such as non-engaging healing and implant abutments, in the implant depends on the expertise of the dentist.

In some cases an angled abutment must be used to support the anatomical layer. In such an abutment the longitudinal axis of the portion on which the anatomical layer is placed has an angle relative to the longitudinal axis of the portion which is inserted into the implant. This may be the case when the implant is titled relative to the sagittal plane of the patient, In such cases it is important that a customized healing abutment is arranged correctly relative to the implant in order to provide that the soft tissue is shaped anatomically correct.

Likewise it may also be important that the implant abutment is arranged correctly relative to the implant in order to provide a good support for the anatomical layer, such as a crown layer or a crown portion of a bridge restoration.

Positioning jigs for confirming that the correct arrangement of a dental restoration in dental implant are known in the prior art. US2008153067 teaches a method for digitally designing an overmould which can be used to ensure a correct positioning of a customized abutment and implant analog in a physical model of a patient's set of teeth.

When a dentist needs access to the implant region while having the positioning jig arranged at the patient's set of teeth, e.g. for securing an implant abutment in the implant using a retention screw, a through hole is drilled in the manufactured positioning jig. This adds a further step to the manufacture of the positioning jig in which step there is a risk of damaging the manufactured jig For the surgical drilling of a bore into the patient's jaw bone for the implant, a drill guide can be manufactured and arranged in the patient's mouth where it guides the dentist to drill the bore at a planned implant placement.

The implant placement can be planned based on a CT scan of the patient's set of teeth showing nerves and roots of neighboring teeth. From the planned position and orientation and the drill guide can be digitally designed and subsequently manufactured using direct digital manufacturing techniques.

SUMMARY

One object of the invention is to provide a method, a user interface and a system for creating a virtual positioning jig for manufacturing a positioning jig which is configured for confirming the correct arrangement of a dental restoration in a dental implant which has been secured in the patient's jaw bone, i.e. that the dental restoration is arranged according to a target arrangement or within an acceptable error margin at the target arrangement. This property makes the positioning jig very useful when positioning the dental restoration in the implant.

One object of the invention is to provide a method, a user interface and a system for creating a virtual positioning jig for manufacturing a positioning jig, where the positioning jig comprises a through hole for providing access to the dental restoration and the implant region through the positioning jig, and where the through hole is defined without the need for post-processing of the manufactured positioning jig.

One object of the invention is to provide a method, a user interface and a system for creating a virtual positioning jig for manufacturing a positioning jig, where the positioning jig comprises a through hole for providing access to the dental restoration through the positioning jig, and where the through hole is defined already in the virtual positioning jig from which the positioning jig is manufactured.

One object of the invention is to provide a method, a user interface and a system for creating a virtual customized healing abutment and a corresponding virtual positioning jig for where the latter is configured to provide that the positioning jig can be used for correct positioning of the customized healing abutment, and where the positioning jig comprises a through hole for providing access to the customized healing abutment through the positioning jig.

One object of the invention is to provide a method, a user interface and a system for creating a virtual drill guide and a corresponding virtual positioning jig for manufacturing a drill guide and a positioning jig, where the drill guide is configured for guiding a dentist when surgically drilling a bore into the jaw bone in an implant region of the patient's set of teeth, and where the positioning jig comprises a through hole for providing access to a dental restoration arranged in an implant secured in the drilled bore. The dental restoration can e.g. be a customized healing abutment designed and manufactured for this implant.

One object of the invention is to provide a method, a user interface and a system for creating a virtual drill guide, and corresponding customized healing abutment and virtual positioning jig for manufacturing a drill guide, customized healing abutment and positioning jig, where the drill guide is configured for guiding a dentist when surgically drilling a bore into an implant region of the patient's set of teeth and where the positioning jig comprises a through hole for providing access to the customized healing abutment when this is arranged in an implant secured in the drilled bore. Such a method, user interface and system can provide that the drill guide, the customized healing abutment and the positioning jig can be designed and subsequently manufactured before the surgical drilling of a bore into the patient's jaw bone, such that all three units are available to the dentist when the surgical drilling procedure is initiated.

Disclosed is hence a method for creating a virtual positioning jig for manufacturing a positioning jig, where said manufactured positioning jig is for use when positioning a manufactured dental restoration at a patient's set of teeth, said method comprising:

obtaining a digital 3D representation of the set of teeth, said digital 3D representation comprising an implant region portion relating to an implant region and a neighbor region portion relating to a neighbor region of the set of teeth;

designing a virtual model of the dental restoration at the digital 3D representation such that the designed virtual dental restoration model is arranged according to a target arrangement relative to the digital 3D representation, said virtual dental restoration model comprising an outer restoration surface;

creating an inner surface and an outer surface of the virtual positioning jig, where the inner jig surface is created based on said outer restoration surface, the target arrangement, and the neighbor region portion of the digital 3D representation; and defining a through hole of the virtual positioning jig at the implant region portion of the digital 3D representation, where the through hole extends from the inner jig surface to the outer jig surface.

Disclosed is hence also a user interface for creating a virtual positioning jig for manufacturing a positioning jig, where said manufactured positioning jig is for use when positioning a manufactured dental restoration relative to a patient's set of teeth, where the user interface is configured for:

visualizing a digital 3D representation of the set of teeth and a designed virtual model of the dental restoration, where said digital 3D representation comprises an implant region portion relating to an implant region and a neighbor region portion relating to a neighbor region of the set of teeth, and where the virtual model of the dental restoration is arranged according to a target arrangement relative to the digital 3D representation, said virtual dental restoration model comprising an outer restoration surface;

creating an inner surface and an outer surface of the virtual positioning jig, where the inner jig surface is created based on said outer restoration surface, the target arrangement, and the neighbor region portion of the digital 3D representation; and defining a through hole of the virtual positioning jig at the implant region portion of the digital 3D representation, where the through hole extends from the inner jig surface to the outer jig surface.

In the context of the present invention, the phrase "implant region" is used in relation to a region of the set of teeth where a dental implant is already located or is to be located. The dental restoration is designed to be arranged at this implant, i.e. to be inserted in the implant and optionally to be secured at the implant using e.g. a retention screw.

In the context of the present invention, the phrases "virtual dental restoration model" and "virtual model of the dental restoration" are used interchangeably.

In the context of the present invention, the phrase "inner jig surface" is used in relation to the inner surface of the virtual positioning jig and in relation to the inner surface of the manufactured positioning jig which faces and/or engages the patient's set of teeth and the manufactured dental restoration when the positioning jig is arranged in the patient's mouth.

The inner jig surface is shaped such that the positioning jig only fits the neighbor region and the dental restoration when the dental restoration is arranged correctly at the implant region. This provides that the positioning jig can be used when positioning the dental restoration to confirm the correct arrangement of the dental restoration, i.e. confirm that the dental restoration is arranged according to the target arrangement.

In some cases there is a range of orientations of the dental restoration around the target arrangement that are acceptable and the inner jig surface may be designed such that for some of these orientations there is no direct contact between the inner jig surface and the outer restoration surface. The inner jig surface is then preferably designed such that there is contact between the dental restoration and the positioning jig at the extremes of this range such that the positioning jig does not fit when the dental restoration is arranged according to an arrangement which is outside said range.

In the context of the present invention, the phrase "outer jig surface" is used in relation to the outer surface of the virtual positioning jig and in relation to the outer surface of the manufactured positioning jig. The outer jig surface faces away from the teeth of the neighbor section and the dental restoration which are contacted by the inner jig surface.

In embodiments where the virtual positioning jig is designed from surfaces of the neighbor section and of the virtual dental restoration model it is contemplated that the virtual dental restoration model is arranged according to its target arrangement at the dental implant.

In a positioning jig manufactured from the created virtual positioning jig, the through hole provides that a retention screw can engage a screw bore of the dental restoration through the manufactured positioning jig when this is arranged at the patient's set of teeth.

It is an advantage that designing of the virtual model of the positioning jig includes the through hole and its position since an additional step of manually forming the through hole after the manufacture of the positioning jig is avoided. There is some risk of a human error when defining the position of the through hole manually either when marking the position of the through hole or when manually generating the through hole by drilling into the material of the positioning jig.

In order to make it possible to manually mark the location of the through hole on a prior art positioning jig it is necessary to fabricate such positioning jigs in transparent materials. With the present invention, a wider range of materials can be used including opaque materials.

A further advantage of the invention compared to methods where the positioning jig is manufactured based on a physical model of the set of teeth is that by virtually defining the through hole of the positioning jig, the physical model of the set of teeth is no longer needed.

According to an aspect of the invention is a method for creating a virtual positioning jig for manufacturing a positioning jig, where said manufactured positioning jig is for use when positioning a manufactured dental restoration correctly relative to a patient's set of teeth, said method comprising:

obtaining a digital 3D representation of the set of teeth, said digital 3D representation comprising an implant region portion relating to an implant region and a neighbor region portion relating to a neighbor region of the set of teeth;

designing a virtual model of the dental restoration at the digital 3D representation such that the designed virtual dental restoration model is arranged according to a target arrangement relative to the digital 3D representation, said virtual dental restoration model comprising a screw bore and an outer restoration surface;

creating an inner surface and an outer surface of the virtual positioning jig, where the inner jig surface is created based on said outer restoration surface, the target arrangement, and the neighbor region portion of the digital 3D representation; and defining a through hole of the virtual positioning jig at the implant region portion of the digital 3D representation, where the through hole extends from the inner jig surface to the outer jig surface.

In some embodiments, the method comprises combining the virtual dental restoration model and the digital 3D representation to obtain a combined virtual model, where the virtual dental restoration model preferably is arranged according to its target arrangement in the combined virtual model. When using a combined virtual model, the virtual positioning jig can be generated in relation to the portions of the combined virtual model corresponding to the dental restoration and to the neighbor region.

In some embodiments, the inner jig surface is virtually created by copying relevant sections of the combined virtual model, i.e. the section of the combined virtual model corresponding to at least a part of the virtual dental restoration model and at least one section of the combined virtual model corresponding to the neighbor region portion of the digital 3D representation of the patient's set of teeth. When the virtual dental restoration model is arranged according to its target arrangement in the combined virtual model this approach has the advantage that in a manufactured positioning jig, the inner surface is immediately configured such that it can confirm the correct arrangement of the dental restoration at the implant region.

When the digital 3D representation and the virtual dental restoration model are arranged together according to the target arrangement they form an assembly with substantially the same surfaces as the combined model.

In some embodiments, the inner jig surface is virtually created by copying relevant sections of the assembly, i.e. by copying at least a part of the virtual dental restoration model and at least one section of the neighbor region portion of the digital 3D representation of the patient's set of teeth. When the virtual dental restoration model is arranged according to its target arrangement in the assembly this approach has the advantage that in a manufactured positioning jig, the inner surface is immediately configured such that it can confirm the correct arrangement of the dental restoration at the implant region.

In some embodiments, the method comprises visualizing the virtual dental restoration model together with the digital 3D representation, where the virtual dental restoration model preferably is arranged according to its target arrangement in this visualization. The visualization may be provided to an operator using a visual display unit, such as a computer screen.

In some embodiments, the method comprises forming a virtual body by connecting corresponding edges of the inner and outer jig surfaces. The edges can e.g. be connected by a loofting procedure in which a connecting surface is formed between the edges. The virtual positioning jig can then be formed by defining the through hole in the virtual body.

In some embodiments, the method comprises defining two or more through holes such that the manufactured positioning jig can be used for a multi-implant case. This can be relevant when producing an implant based denture which is designed to e.g. be secured at four implants in the patient's upper or lower jaw. For such applications non-engaging abutments are often preferred and the method of the invention allows for the manufacture of a positioning jig which can confirm that one or more of these abutment are arranged according to their target arrangements.

In some embodiments, designing said virtual dental restoration model comprises defining a screw bore such that a dental restoration manufactured from the virtual model dental restoration model can be attached to said dental implant using a retention screw configured for engaging said screw bore.

In some embodiments, the method comprises identifying the position and orientation of a dental implant in the patient's jaw bone.

In some cases the implant is already secured in the patient's jaw bone when the digital 3D representation of the patient's set of teeth is obtained and the virtual positioning jig is created. In such cases it may be possible to identify the position and orientation of the dental implant from the digital 3D representation. When the digital 3D representation is obtained by a direct 3D surface scanning of the patient's set of teeth using an intra-oral scanner the implant location and orientation can be derived using a scan-abutment arranged in the dental implant during the scanning.

The implant location and orientation can also be derived from a CT scanning of the patient's set of teeth in which the part of the implant which is located below the surface can be seen.

One advantage of identifying the implant position and orientation is that this information can be used in the designing of the dental restoration, e.g. a customized healing abutment, a monolithic screw retained crown, or an implant abutment, as well as in designing anatomical layers which are to be arranged at such an implant abutment.

In cases where the through hole is designed to allow the dentist to secure an implant abutment in the implant using a retention screw which engages a screw bore of the dental restoration, the through hole can be defined based on the implant position and orientation and it is hence advantageous to identifying the implant position and orientation in the patient's jaw bone.

In some embodiments, the method comprises planning the position and/or orientation of a dental implant in the patient's jaw bone.

The implant position and/or orientation can be planned by inspecting a CT scan of the patient's set of teeth in which the inferior alveolar nerve and the roots of the teeth in the neighbor region can be seen. Several commercially available software packages provide tools for determining an acceptable position and orientation of the implant in the jaw bone where there is no risk of contact with the nerve or teeth roots.

The CT scan may be part of the obtained digital 3D representation of the patient's set of teeth or it may be an additional scan in cases where the digital 3D representation is a surface scan, such as a scan using an optical scanner.

In some embodiments, the method further comprises creating a virtual drill guide for manufacturing a drill guide based on the planned implant position and orientation. The drill guide is configured for guiding a dentist when surgically drilling a bore for the implant into the jaw bone at the implant region in such a manner that when the implant is arranged in said drilled bore it is substantially arranged according to the planned position and orientation. From created virtual drill guide a drill guide can subsequently be manufactured using direct digital manufacturing techniques.

When the dental restoration comprises or is a virtual customized healing abutment it can be created based on the same planned position and orientation of the implant from which the drill guide is designed. When the customized healing abutment is designed, the inner surface of the virtual positioning jig can be created, e.g. by copying the outer surface of the customized healing abutment, and the outer jig surface can be created by e.g. a shelling of the inner jig surface. Subsequently the through hole of the positioning jig can be virtually defined based on the planned implant position and orientation and on the outer surface of the created virtual customized healing abutment.

One advantage of this approach is that the drill guide, the customized healing abutment and the positioning jig are created to automatically cooperate. When the bore is surgically drilled into the jaw bone using the drill guide, the customized healing abutment is already shaped such that it can form the gingiva according to the preferred gingiva profile, and the correct arrangement of the customized healing abutment in the implant can be confirmed by the positioning jig.

Disclosed is a kit comprising a positioning jig, a customized healing abutment and a surgical drill guide, where the drill guide is configured for guiding a dentist when surgically drilling a bore into the bone at an implant region of the patient's set of teeth and where the positioning jig comprises a through hole for providing access to the customized healing abutment when this is arranged in an implant secured in the drilled bore. The positioning jig is configured for confirming that the customized healing abutment is correctly arranged in the implant such it can shape the soft tissue according to a preferred gingiva profile.

In some embodiments, the target arrangement of said virtual dental restoration model relative to said digital 3D representation is determined from the identified or planned position and orientation of the dental implant. When the dental restoration is arranged according to its target arrangement it is considered to be arranged correctly relative to the patient's set of teeth, i.e. the target arrangement represents a correct arrangement of the dental restoration in the patient's set of teeth.

The though hole provides a virtual passage to the implant region portion when the virtual positioning jig is arranged relative to the digital 3D representation or relative to the combined virtual model, such that for a manufactured positioning jig, the through hole provides a passage to the implant region, where the passage allows physical contact with the manufactured dental restoration arranged at the implant region through the positioning jig.

In some embodiments, the arrangement of the through hole of the virtual positioning jig is determined based on the planned or identified position and orientation of the dental implant.

This is advantageous since the position and orientation of the dental implant in many cases determines the insertion direction a retention screw used securing the dental restoration at the implant. Taking into account the position and orientation of the dental implant can ensure that the through hole is arranged such that the retention screw can engage the dental restoration through it.

In some embodiments, a cross-sectional diameter of the through hole of the virtual positioning jig is determined from a known diameter of the retention screw and/or from a predetermined diameter.

When the dental restoration is e.g. an implant abutment and a retention screw is used for securing the implant abutment at the dental implant, the cross-sectional diameter may be selected to be only slightly larger (e.g. 1 mm larger) than the diameter of the retention screw such that in the manufactured positioning jig the through hole can guide the retention screw towards the implant abutment at the dental implant. The cross-sectional diameter may be selected to be substantially larger (e.g. 5-10 mm larger) than the diameter of the retention screw such that in the manufactured positioning jig there is room for the dentist to arrange the retention screw e.g. in an implant abutment secured in the implant.

In some embodiments, a cross-sectional diameter of the through hole of the virtual positioning jig is selected by an operator.

This provides that the operator can select a cross-sectional diameter according to his or hers preferences.

Preferably, the cross-sectional diameter of the through hole is sufficiently large to allow an implant screw to engage the dental implant below the manufactured positioning jig.

In some embodiments, the method comprises determining an insertion volume, such as an insertion volume for the retention screw. The insertion volume may be configured to provide the necessary space for the retention screw to approach and engage the implant in the implant region below the manufactured positioning jig.

In some embodiments, the insertion volume for the retention screw is determined from the planned or identified position and orientation of the dental implant and/or from the designed virtual dental restoration model. In some embodiments, the insertion volume is defined as a cylindrical structure which is aligned with the longitudinal axis of the implant which again is aligned with the screw bore of the dental restoration.

In some embodiments, the through hole of the virtual positioning jig is defined by a Boolean subtraction of the insertion volume from the formed virtual body.

Using an insertion volume which is determined from the position and orientation of the dental implant to define the through hole of the virtual positioning jig is advantageous since it can ensure that when the manufactured positioning jig is arranged at the patient's teeth the through hole is arranged such that a retention screw can engage the dental restoration and/or the dental implant through it.

In some embodiments, the implant region of the set of teeth relates to a region comprising a damaged or dead tooth, gingiva at this tooth, a dental implant, a healing abutment, or gingiva covering a location where a tooth normally would be present.

In some embodiments, the neighbor region of the set of teeth comprises one or more neighbor teeth on which the manufactured positioning jig can rest when arranged at the patients set of teeth. The neighbor region portion of the digital 3D representation then comprises a virtual surface relating to this at least one tooth. This virtual surface can then be used when creating the part of the inner surface of the positioning jig which is designed to engage the teeth of the neighbor region. When the inner surface of the virtual positioning jig matches the corresponding part of the digital 3D representation, the inner surface of the manufactured positioning jig matches the surface of the patient's teeth and the positioning jig is automatically arranged at its correct location when placed at the patient's teeth.

In some embodiments, the neighbor region of the set of teeth is adjacent to and/or surrounds the implant region.

In some embodiments, the method comprises generating a positioning jig 3D spline in relation to the digital 3D representation and/or in relation to the virtual dental restoration model and/or in relation to the combined virtual model and/or in relation to the formed virtual body. Such as 3D spline can be generated by the user defining points on e.g. the combined virtual model which the 3D spline extends between. These points can be defined using e.g. a computer mouse connected to a personal computer comprising software for implementing the method according to the present invention.

In some embodiments, at least part of a boundary of the inner jig surface is defined by the positioning jig 3D spline.

In the context of the present invention, the phrase "boundary" when used in relation to the virtual positioning jig or in relation or a part of the virtual positioning jig, such as e.g. the inner jig surface, refers to a section of the virtual positioning jig which defines the perimeter of the manufactured positioning jig facing the corresponding jaw bone when it is arranged in relation to the patient's set of teeth.

Using a positioning jig 3D spline to define the boundary of the inner jig surface allows an operator to define the boundary of the contact between the manufactured positioning jig and the patient's set of teeth according to his or hers preferences. Some operators wish to have the boundary close to the patient's gingiva while others prefer to have a safe distance to the pressure sensitive soft tissue of the gingiva.

In some embodiments, the positioning jig 3D spline comprises a dental restoration section which is shaped according to the outer restoration surface of the virtual dental restoration model.

In the context of the present invention, the phrase "shaped according to the outer restoration surface" is used to describe the case where the corresponding section of the positioning jig 3D spline is configured to follow the outer surface of the designed dental restoration. The section of the positioning jig 3D spline may coincide with the outer restoration surface or be offset while still maintaining the geometry of the surface. Providing such an offset may be advantageous when there is a range of correct arrangements of the dental restoration such that there is some room for e.g. rotating the dental restoration in the implant.

In some embodiments, the positioning jig 3D spline comprises a neighbor section which is shaped according to the neighbor region portion of the digital 3D representation.

In the context of the present invention, the phrase "shaped according to the neighbor region portion" is used to describe the case where the corresponding section of the positioning jig 3D spline is configured to follow a surface in the neighbor region portion of the digital 3D representation of the set of teeth. The section of the positioning jig 3D spline may coincide with the surface it follows or be offset while still maintaining the geometry of the surface.

Preferably, the dental restoration section has a segment on the lingual side of the virtual dental restoration model and a segment on the buccal/labial side.

Preferably, the neighbor section has at least one segment on the lingual side of the neighbor region portion and at least one segment on the buccal/labial side of this portion.

The lingual segment of the dental restoration section can then be connected with the lingual segment or segments of the neighbor section, while the buccal/labial segment of the dental restoration section can be connected with the buccal/labial segment or segments of the neighbor section In some embodiments, the method comprises defining control points in relation to the digital 3D representation and in relation to the virtual dental restoration model, and generating the positioning jig 3D spline from these control points.

Control points for the dental restoration section of the positioning jig 3D spline may then be defined in relation to the outer restoration surface of the virtual dental restoration model while control points for the neighbor section of the positioning jig 3D spline may be defined in relation to the neighbor region portion of the digital 3D representation.

In some embodiments, at least part of the neighbor section of the positioning jig 3D spline is shaped according to a line defined by an offset of a gingival margin of teeth in said neighbor region portion of the digital 3D representation.

The offset can be along the surface of the teeth in the neighbor region portion and away from the gingiva such that when the positioning jig 3D spline is used to define the boundary of the positioning jig, the offset provides that contact between the positioning jig and the sensitive gingiva is avoided when the positioning jig is arranged at the patient's set of teeth.

In some embodiments, the method comprises connecting the dental restoration section and the neighbor section of the positioning jig 3D spline to form the positioning jig 3D spline.

The dental restoration is preferably a unit configured for engaging a dental implant, such as a monolithic crown, a customized healing abutment or an implant abutment.

In some embodiments, the dental restoration comprises an implant abutment The outer restoration surface is then the outer surface of the implant abutment, i.e. the surface of the implant abutment configured for facing an anatomical layer such as a crown and/or coping designed for the implant abutment. When the positioning jig is used in relation to an implant abutment it is often referred to as an abutment jig.

In some embodiments, the dental restoration is an implant abutment.

Additional units may then be designed and manufactured to be arranged in relation to the implant abutment in order to obtain a full restoration, such as a coping and a crown, a denture or a pontic of a bridge designed to engage the implant abutment.

The design of the virtual model of the implant abutment often takes into account the position and orientation of the implant, either as the planned or as the determined position and orientation of the implant. Further the design step can take into account the neighbor region portion of the digital 3D representation of the set of teeth, e.g. by designing the outer surface of a crown which is to be arranged at the implant abutment and using the designed crown outer surface in the designing of the implant abutment. For instance there are some constraints on the minimum thickness of such a crown in order to ensure that it is mechanically robust and these constraints can define limitations in the size and form of the implant abutment given that there is a limited space available at the implant region. Further it may be advantageous to confirm that there exists an insertion path along which the crown can be moved to the implant abutment and if this is not the case, a redesign of the implant abutment can be sufficient to provide that such an insertion path exists.

In many cases, the implant abutment and the dental implant have a preferred relative arrangement and the virtual positioning jig is then designed to provide guidance to this preferred arrangement.

In some embodiments, the positioning jig 3D spline is shaped according to a finish line of the implant abutment or of the customized healing abutment, or according to a line defined by an offset of said finish line, such as by an offset towards the occlusal plane of the teeth. Such an offset provides that contact between the manufactured positioning jig and the sensitive gingiva is avoided when the positioning jig is arranged at the patient's set of teeth. The offset is preferably such that the offset line still follows the outer restoration surface of the virtual dental restoration model.

In some embodiments, the dental restoration comprises a customized healing abutment. The customized healing abutment is for being arranged in the implant during osseointegration and preferably comprises a part configured for engaging a dental implant arranged in a bore drilled into the jaw bone and a part that contacts the soft tissue of the implant region when the customized healing abutment is arranged in the implant. In some cases the outer surface of the customized healing abutment, which contacts the surrounding gingiva during the osseointegration, is shaped to form the soft tissue according to a preferred gingiva profile. It is then advantageous to ensure that the customized healing abutment is arranged according to its target arrangement which can be provided using the positioning jig. Often the upper part of the customized healing abutment, i.e. the part which contacts the gingiva, is not symmetric and the customized healing abutment must be arranged correctly in order to shape the gingiva according to the preferred profile.

In some embodiments, a preferred gingiva profile at the implant region is determined. This can be done either by selecting a profile from a library or by virtually designing the gingiva profile. The surface of the customized healing abutment which is configured for contacting the gingiva in the implant region can then be designed based on the preferred gingiva profile such that the customized healing abutment shapes the gingiva to this profile during the osseointegration.

Creating the customized healing abutment may further comprise identifying the position and orientation of the dental implant and shaping the customized healing abutment such that the relative arrangement of the gingiva contacting surface and the part configured for engaging the implant provides that when the customized healing abutment is arranged at the implant, the gingiva facing surface is aligned correctly with the gingiva, i.e. aligned such that it can shape the gingiva according to the preferred gingiva profile.

In some embodiments, the dental restoration is a customized healing abutment

In some embodiments, the dental restoration comprises a monolithic screw retained crown. When using a positioning jig 3D spline, the dental restoration section of the positioning jig 3D spline may be shaped according outer surface of the monolithic screw retained crown.

In some embodiments, the dental restoration section of the positioning jig 3D spline is shaped according to a gingiva facing portion of the outer surface of the dental restoration such that at least a part of the positioning jig 3D spline follows the gingiva facing portion.

In some embodiments, at least part of the dental restoration section is shaped according to a line defined by an offset of said gingiva facing portion, such as by an offset towards the occlusal surface of the virtual dental restoration model. The offset is preferably such that the line still follows the outer restoration surface of the virtual dental restoration model.

In some embodiments, the inner jig surface and the outer jig surface are created in one common step, such that the surfaces at least partly are created simultaneously.

In some embodiments, the inner jig surface and the outer jig surface are created in separate steps, such that one surface at least partly is created before the other.

In some embodiments, the inner jig surface at the implant region is formed by a Boolean addition of the implant region portion of the digital 3D representation and the designed virtual dental restoration model.

In the context of the present invention, the surface provided by a Boolean addition of a first and a second surface may correspond to the surface of a solid structure formed by a logical disjunction of the solid structures with surfaces according to the first and second surface. In cases where the implant region portion of the digital 3D representation has been sectioned out, a lofting step connecting the implant region portion of the digital 3D representation and the designed virtual dental restoration model may be required.

In some embodiments, the method comprises shelling said inner jig surface.

In some embodiments, the outer jig surface is created by a shelling of the inner jig surface.

In some embodiments, creating the inner and the outer surface of the virtual positioning jig comprises defining a virtual bar structure in relation to the digital 3D representation and the virtual dental restoration model or in relation to the combined virtual model.

The virtual bar structure is preferably shaped such that it follows the arch of the set of teeth in the implant and neighbor region portions when virtually arranged in relation to the digital 3D representation of the set of teeth or in relation to the combined model.

In some embodiments, creating the inner jig surface and the outer jig surface comprises a Boolean subtraction of the assembly of the digital 3D representation and the virtual dental restoration model from the virtual bar structure or a subtraction of the combined virtual model from the virtual bar structure.

The Boolean subtraction of the virtual volumes of these units may correspond to determining the relative complement of the units, such that the inner jig surface and the outer jig surface at least in part can be created by determining the relative complement of said assembly or of the combined virtual model in the virtual bar structure. At the implant region portion the inner jig surface is then at least in part created by determining the relative complement of the virtual dental restoration model in the virtual bar structure, while at the neighbor region portion the inner jig surface is then at least in part created by determining the relative complement of the neighbor region portion of the digital 3D representation in the virtual bar structure. The outer jig surface may be defined directly by the outer surface of the virtual bar structure.

In some embodiments, a boundary of the virtual bar structure is defined by said positioning jig 3D spline. The virtual bar structure may then be cut to the positioning jig 3D spline, i.e. part of the virtual bar structure arranged further away from the occlusal surface of the teeth than the positioning jig 3D spline is virtually removed.

In some embodiments, the height and the length along the dental arch of the virtual bar structure is selected by an operator. The height and the length of the virtual bar structure can be selected by the operator by his choice of shape of the positioning jig 3D spline.

In some embodiments, the virtual bar structure is selected from a bar structure library.

In some embodiments, the virtual positioning jig is designed with a retention structure configured for releasable securing the dental restoration in the manufactured positioning jig.

In some embodiments, the virtual dental restoration model is designed with mating structure configured for mating with the retention structure of the positioning jig.

The retention structure and the mating structure are preferably designed to ensure that the dental restoration can be held by the manufactured positioning jig while still being able to be released therefrom.

In some embodiments, the method comprises sectioning a portion out of the digital 3D representation of the teeth at the implant region portion. The portion of the digital 3D representation which is sectioned out may correspond to a damaged or dead tooth.

In some embodiments, a diagnostic wax-up for the set of teeth is created. The inner jig surface can then be created based on said diagnostic wax-up. The diagnostic wax-up shows a desired arrangement and shape of the teeth in the implant region and optionally also shows teeth of the neighbor region. Creating a diagnostic wax-up may involve designing a virtual model for a tooth in the implant region. If the dental restoration is a monolithic screw retained crown, the inner jig surface can be created directly from the surface of the designed monolithic screw retained crown. If the dental restoration is an implant abutment, the surface of the implant abutment is designed from the diagnostic wax-up and the inner jig surface is created based on the designed implant abutment surface. When designing monolithic screw retained crown or an implant abutment, the orientation and position of the dental implant may be taken into account. This may be a planned orientation and position of the dental implant, such as an orientation and position planned from the diagnostic wax-up or from the obtained digital 3D representation of the set of teeth.

In some embodiments, at least some steps of the method are computer implemented.

In some embodiments said digital 3D representation is obtained at least in part by loading the digital 3D representation into a data processing system.

In some embodiments the method comprises controlling the undercuts at the neighbor tooth or teeth in the neighbor region and/or at the dental restoration. A controlled undercut has the advantage that a controlled retention of the manufactured positioning jig at the patient's set of teeth can be obtained. With a slight undercut of e.g. 1 mm the positioning jig can to some extend releasable secure itself of the teeth in the neighbor region.

In some embodiments, the digital 3D representation is obtained by an intra-oral scanning of at least part of the patient's set of teeth, a scanning of at least part of an impression of the patient's set of teeth, and/or a scanning of at least part of a model of the patient's set of teeth.

The digital 3D representation of the patient's set of teeth may be obtained for all the teeth in the upper and/or lower jaw of the patient or a part of these teeth.

In some embodiments, the 3D scanning is performed by means of laser light scanning, white light scanning, probe-scanning, X-ray scanning, and/or CT scanning.

The intra-oral scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

3D modeling is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

Disclosed is method for manufacturing a positioning jig, where said manufactured positioning jig is for use in positioning a dental restoration at a patient's set of teeth, said method comprising:
  creating a virtual positioning jig using the method according to any of the embodiments; and
  manufacturing the positioning jig based on the virtual positioning jig by direct digital manufacturing.

In some embodiments, the direct digital manufacturing comprises 3D printing or 3D milling.

Disclosed is a computer program product comprising program code means for causing a data processing system to perform the method of any one of the embodiments, when said program code means are executed on the data processing system.

In some embodiments, the computer program product comprises a computer-readable medium having stored there on the program code means.

Disclosed is a non-transitory computer readable medium storing thereon a computer program, where said computer program is configured for causing computer-assisted creation of a virtual positioning jig for manufacturing a positioning jig using the method according to any of the embodiments.

Disclosed is a system for creating a positioning jig wherein the system comprises a non-transitory computer readable medium having one or more computer instructions stored thereon, where said computer instructions comprises instructions for creating a virtual positioning jig for manufacturing a positioning jig using the method according to any of the embodiments.

The present invention relates to different aspects including the method and system described above and in the following, and corresponding methods, and systems, each yielding one or more of the benefits and advantages described in connection with the first mentioned aspect, and each having one or more embodiments corresponding to the embodiments described in connection with the first mentioned aspect and/or disclosed in the appended claims.

In some embodiments, the user interface is configured for designing the virtual model of the dental restoration at the digital 3D representation, where the dental restoration may be a customized healing abutment.

In some embodiments, user interface is configured for designing a drill guide for guiding a dentist when drilling a bore for the implant into the jaw bone at the implant region.

Disclosed is a method for virtually creating a drill guide, a customized healing abutment and a positioning jig for manufacturing a drill guide, a customized healing abutment and a positioning jig, said method comprising:
  obtaining a digital 3D representation of the set of teeth, said digital 3D representation comprising an implant region portion relating to an implant region and a neighbor region portion relating to a neighbor region of the set of teeth;
  planning the position and orientation of a dental implant in the patient's set of teeth
  creating a virtual drill guide for manufacturing a drill guide for guiding a dentist when surgically drilling a bore for the dental implant into the jaw bone at the implant region, such that when an implant is arranged in said drilled bore it is substantially arranged according to the planned position and orientation,
  designing a virtual model of the dental restoration at the digital 3D representation such that the designed virtual dental restoration model is arranged according to a target arrangement relative to the digital 3D representation, said virtual dental restoration model comprising an outer restoration surface, wherein the dental restoration comprises a customized healing abutment comprising a part configured for engaging the dental implant arranged in the drilled bore and a part that can form the gingiva of the implant region according to a preferred gingiva profile when the customized healing abutment is arranged according to the target arrangement;
  creating an inner surface and an outer surface of the virtual positioning jig, where the inner jig surface is created based on said outer restoration surface, the target arrangement, and the neighbor region portion of the digital 3D representation; and
  creating the virtual positioning jig from the inner and outer jig surface; such that the positioning jig can confirm that the customized healing abutment is arranged according to the target arrangement.

In some embodiments, the method comprises defining a through hole of the virtual positioning jig at the implant region portion of the digital 3D representation, where the through hole extends from the inner jig surface to the outer jig surface such that in the manufactured positioning jig the through hole provides access to the implant region through the positioning jig.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 8A-8D illustrate how the inner and outer jig surfaces can be generated using a virtual bar structure.

DETAILED DESCRIPTION

In the following description, reference is made to the accompanying figures, which show by way of illustration how the invention may be practiced.

Figure 1:
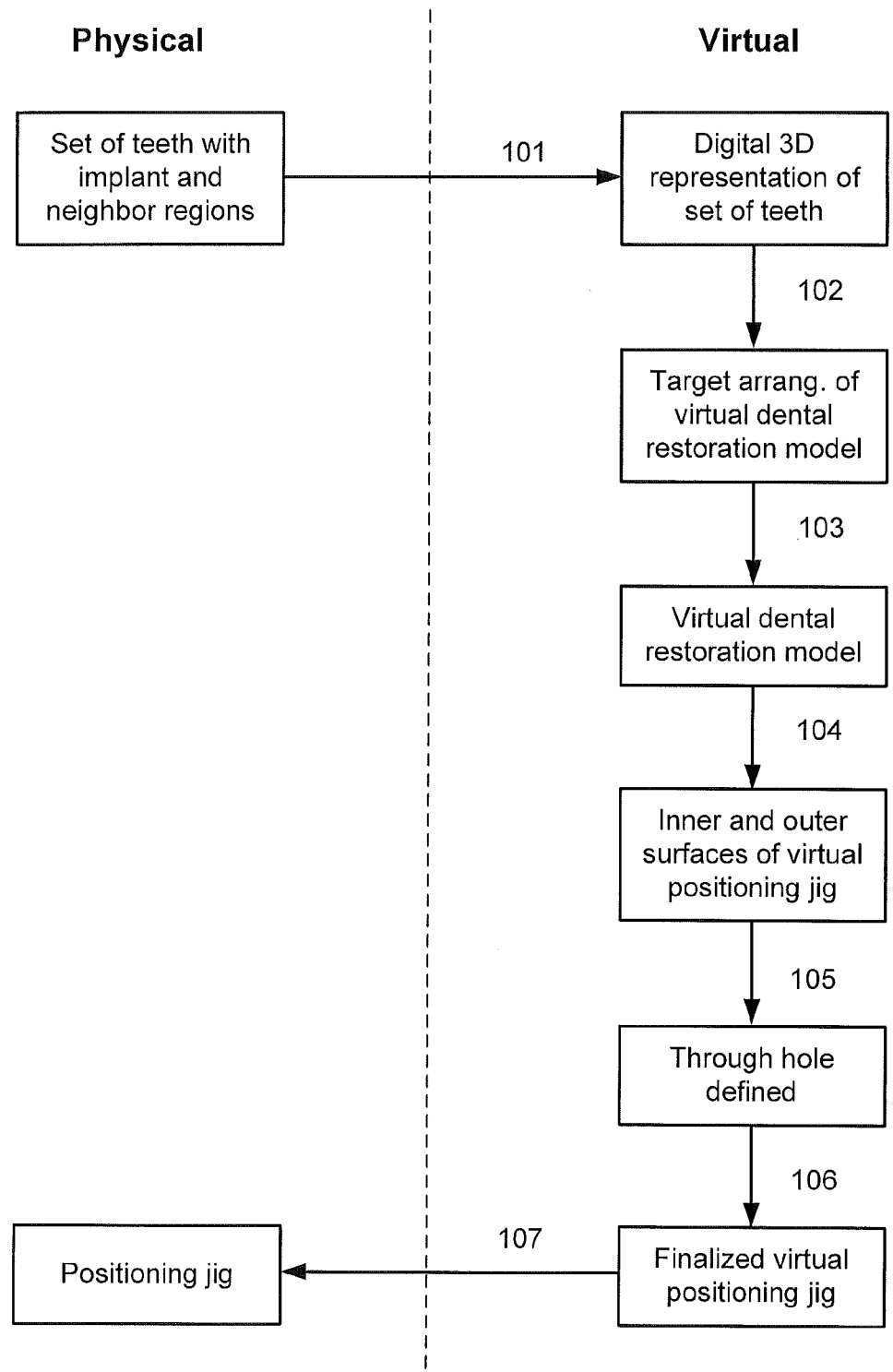
FIG. 1 shows a flow chart of an embodiment of the invention.

FIG. 1 shows a flow chart of a method for creating a virtual positioning jig and manufacturing a positioning jig from the created virtual positioning jig. In the flow chart 100, the left hand side relates to physical units such as the patient's set of teeth and a manufactured positioning jig. The right-hand side relates to virtual/digital units such as virtual models of the dental restoration and of the positioning jig.

In step 101, a digital 3D representation of the patient's set of teeth is obtained. For a computer-implemented method the digital 3D representation can be obtained by loading it into a data processing system on which the method is implemented. The digital 3D representation may be a result of a 3D scanning the set of teeth using e.g. an intra-oral scanner for direct 3D scanning of the teeth or by a 3D scanning of an impression or a physical model of the set of teeth.

The set of teeth comprises an implant region for or with a dental implant in which the manufactured dental restoration is to be secured using e.g. a retention screw. The set of teeth further comprises a neighbor region of the set of teeth which e.g. surrounds the implant region and/or is adjacent to the implant region. The 3D scanning of the set of teeth is such that the obtained digital 3D representation comprises an implant region portion relating to the implant region and a neighbor region portion relating to the neighbor region of the set of teeth.

In step 102, the target arrangement of the virtual dental restoration model relative to said digital 3D representation of the set of teeth is identified.

The target arrangement is identified from the planned or identified location and orientation of the dental implant in the digital 3D representation of the set of teeth. In a direct 3D scanning of the patient's set of teeth using an intra-oral scanner the implant location and orientation can be derived using a scan-abutment arranged in the dental implant during the scanning. In a 3D scanning of a physical model of the patient's set of teeth the implant location and orientation can be derived by transferring an impression analog from the dental implant to an impression material used for taking an impression of the patient's set of teeth. An implant analog is then arranged at the impression analog when the physical model is made from the impression such that the implant analog is arranged in the physical model similar to how the implant is arranged in the patient's set of teeth. In a 3D scanning of the physical model of the patient's set of teeth the implant location and orientation can be derived using a scan body arranged in the implant analog during the scanning.

The space available for the dental restoration at the implant region may also be taken into account when identifying the target arrangement of the dental restoration. The available space can determined from the surfaces of the neighbor region portion, such as the surfaces of the teeth in the neighbor region portion and the insertion direction of the dental restoration at the implant region.

In step 103, a virtual model of the dental restoration is designed at the digital 3D representation with the designed virtual dental restoration model arranged according to its target arrangement. The virtual dental restoration model comprises a screw bore and an outer restoration surface. The screw bore is configured to provide access for a retention screw to the screw thread cavity of the dental implant when the dental restoration is inserted at the dental implant. When the dental restoration is an implant abutment, further units such as a coping and/or a crown may be designed such that they are configured to be arranged in relation to the outer restoration surface, i.e. in relation to the outer surface of the implant abutment.

When the virtual dental restoration model is designed at the target arrangement relative to the digital 3D representation of the set of teeth, the method can comprise a step in which the virtual dental restoration model and the digital 3D representation of the set of teeth are combined to obtain a combined virtual model. The virtual dental restoration model is then arranged according to its target arrangement in this combined virtual model.

In step 104, the inner and outer surfaces of the virtual positioning jig are created. The inner jig surface is created based on said outer restoration surface, the target arrangement, and the neighbor region portion of the digital 3D representation. This can be realized in various manners such as by use of a positioning jig 3D spline or a virtual bar structure as described in relation to FIGS. 2 and 3, respectively.

The portion of the inner jig surface which in the manufactured positioning jig is intended for contacting the dental restoration can be created by copying the part of the combined model corresponding to the dental restoration or by an offset of this part. The portion of the inner jig surface which in the manufactured positioning jig is intended for engaging the neighbor region of the set of teeth can be created by copying the corresponding part of the combined model such as by copying a part of the teeth and/or gingiva in this neighbor region portion of the digital 3D representation of the set of teeth.

In step 105, a through hole of the virtual positioning jig is defined at the implant region portion of the digital 3D representation. The through hole is defined such that it extends from the inner jig surface to the outer jig surface.

In step 106, the virtual positioning jig is finalized such that a positioning jig can be manufactured from the virtual positioning jig. In cases where the created inner and outer surfaces of the virtual positioning jig are not automatically connected when created, the finalizing may comprise connecting these surfaces e.g. by a loofting process.

The virtual positioning jig is then created and can be used for manufacturing the positioning jig.

In step 107 the positioning jig is manufactured from the finalized model of the virtual positioning jig using direct digital manufacturing equipment such as a 3D printer or a milling machine.

The order of the steps may be varied to some extent. For instance may an insertion volume used for defining the through hole be defined before the inner jig surface and/or before the outer jig surface. In the described workflow with step 105 being performed before step 106, the through hole is defined before the inner and outer jig surfaces are connected. Alternatively, a virtual body is formed by connecting corresponding edges of the inner and outer surfaces, e.g. by a loofting procedure forming a surface between the edges, before the through hole is defined. The through hole can then subsequently be defined in the virtual body whereby a finalized virtual positioning jig is obtained.

Figure 2:
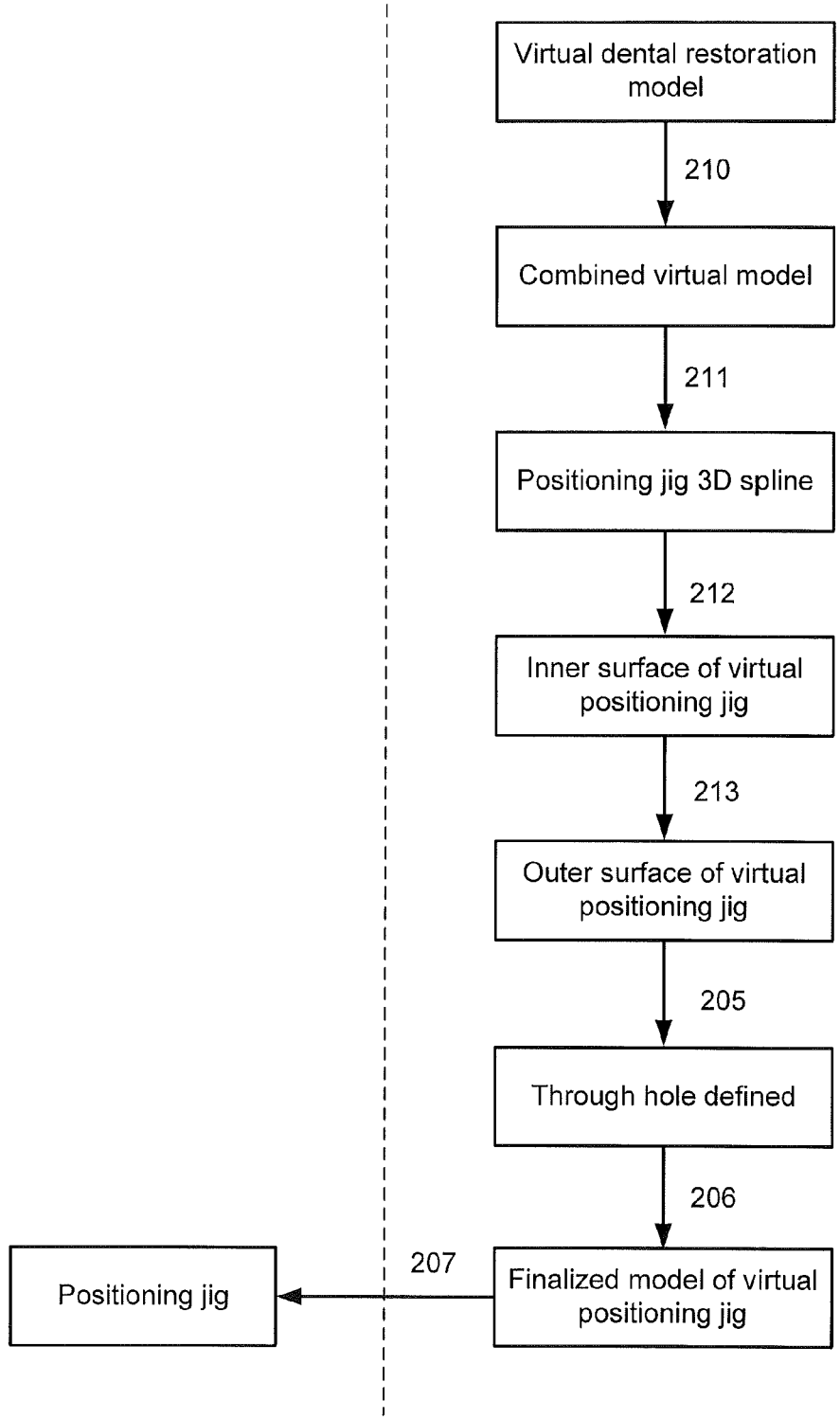
FIG. 2 shows a flow chart where the inner surface of the virtual positioning jig is created using a positioning jig 3D spline.

FIG. 2 shows a flow chart 200 for designing and manufacturing a positioning jig where the inner jig surface is created using a positioning jig 3D spline and the outer jig surface is created by a shelling process.

When the virtual dental restoration model is designed at the target arrangement relative to the digital 3D representation of the set of teeth, the method can comprise a step 210 in which the virtual dental restoration model and the digital 3D representation of the set of teeth are combined to obtain a combined virtual model. The virtual dental restoration model is then arranged according to its target arrangement in this combined virtual model.

In step 211, a positioning jig 3D spline is generated in relation to the portions of the combined virtual model corresponding to the neighbor region of the digital 3D representation and to the virtual dental restoration model. A dental restoration section of the positioning jig 3D spline is shaped according to the outer restoration surface of the virtual dental restoration model while a neighbor section is shaped according to the neighbor region portion, such as shaped according to teeth in the neighbor region of the set of teeth. The tooth surfaces in the neighbor region can be identified in a visual representation of the digital 3D representation, such as in a visual representation provided on a computer screen, or be identified using computer implemented algorithms.

The generated positioning jig 3D spline encloses both the neighbor region portion of the 3D representation and the outer restoration surface of the virtual dental restoration model.

In step 212, the inner surface of the virtual positioning jig model is shaped according to the corresponding surface of the combined virtual model. I.e. at the neighbor region portion, the inner jig surface is shaped according to the surface of the teeth in this region, while at the virtual dental restoration model, the inner jig surface is shaped according to the outer restoration surface. The inner jig surface may be shaped to coincide with the outer restoration surface, e.g. by copying the relevant areas of the outer restoration surface, or shaped to have an offset of the outer restoration surface, e.g. by copying the relevant surface and providing an offset to the copy. The boundary of the inner jig surface is defined by the generated positioning jig 3D spline.

The order of these steps can be varied. The inner jig surface may be generated before the positioning jig 3D spline such that when the positioning jig 3D spline is generated it defines the boundary of the inner jig surface by virtually cutting away areas arranged outside the positioning jig 3D spline. The positioning jig 3D spline may be generated before the inner jig surface, such that the inner jig surface immediately can be generated within the boundary set by the positioning jig 3D spline.

As an alternative to the combined model approach the virtual dental restoration model and the digital 3D representation can be two independent units which are arranged relative to each other according to the target arrangement. The sections of the positioning jig 3D spline can then be defined in relation to the virtual dental restoration model and the digital 3D representation, respectively. These sections can then be combined to obtain the positioning jig 3D spline. From the obtained digital 3D representation of the set of teeth and the designed virtual dental restoration model the inner surface of the virtual positioning jig is created and its boundary is defined by the positioning jig 3D spline.

In step 213 the outer surface of the virtual positioning jig is created by shelling the inner jig surface, where the shelling process defines the outer jig surface as a surface which is offset away from the digital 3D representation of the set of teeth and the designed virtual dental restoration model or from the combined virtual model.

Together steps 210, 211, 212 and 213 forms at least part of step 104 of FIG. 1.

In step 205, the through hole of the virtual positioning jig is defined at the implant region portion of the digital 3D representation or of the combined virtual model. The through hole is defined such that it extends from the inner jig surface to the outer jig surface.

The virtual positioning jig can then be finalized in step 206 by e.g. connecting the inner and outer surfaces of the virtual positioning jig. This can be done by a loofting process which forms a surface between the boundaries/edges of the inner and outer jig surfaces.

The virtual positioning jig is then created and can be used for manufacturing the positioning jig.

The positioning jig manufactured from the virtual positioning jig by direct digital manufacturing in step 207. When the manufactured positioning jig is arranged at the patient's set of teeth, the through hole provides access to the implant region such that the dentist e.g. can insert a retention screw which secures the manufactured dental restoration at the implant.

Figure 3:
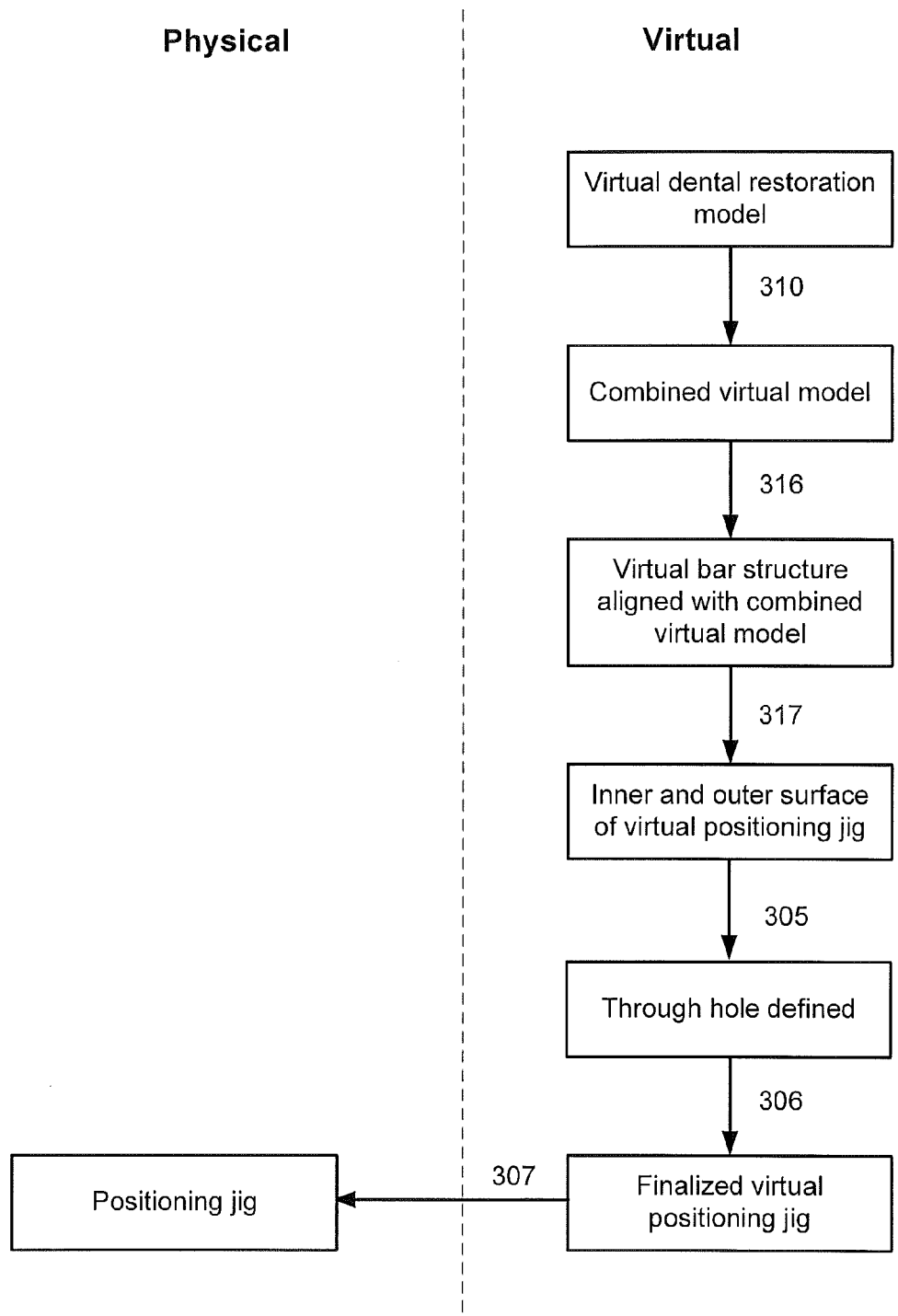
FIG. 3 shows a flow chart where the inner and outer surfaces of the virtual positioning jig are created using a virtual bar structure.

FIG. 3 shows a flow chart 300 where the inner and outer surfaces of the virtual positioning jig are created using a virtual bar structure.

In step 310 a combined virtual model of the virtual dental restoration model and the digital 3D representation of the set of teeth is generated. The virtual dental restoration model is designed at the target arrangement relative to the digital 3D representation of the set of teeth such that in the combined virtual model, the virtual dental restoration model and the digital 3D representation are arranged according to the target arrangement.

In step 316, a virtual bar structure is aligned with the combined virtual model such that the virtual bar structure follows the arch of the set of teeth and such that the outer restoration surface of the virtual dental restoration model at least partly is enclosed by the virtual bar structure. The virtual bar structure may be configured to at least partly enclose the teeth of the neighbor region portion, such as configured to enclose the teeth at their occlusal surface and/or at least part of the buccal/lingual surfaces of the teeth.

In step 317, a Boolean subtraction of the combined virtual model from the virtual bar structure is used for creating at least part of the inner surface of the virtual positioning jig. The Boolean subtraction corresponds to determining the relative complement of the combined virtual model in the virtual bar structure. The Boolean subtraction provides that the inner jig surface is shaped according to the shape of the teeth at the neighbor region portion and according to the virtual dental restoration model at the implant region portion. The outer surface of the virtual positioning jig is defined directly from the outer surface of the virtual bar structure.

The boundary of the virtual positioning jig can be determined directly from the shape of the virtual bar structure or from a 3D spline marking the boundary, such as the positioning jig 3D spline. This 3D spline can mark the boundary on the virtual bar structure itself or on the combined virtual model. The virtual bar structure is then adjusted to fit inside the 3D spline using e.g. computer implemented algorithms.

With this approach, the created virtual positioning jig has the shape of a modified form of the virtual bar structure with the modified virtual bar structure having an inner surface shaped to contact the set of teeth and the dental restoration.

Together steps 310, 316, and 317 forms at least part of step 104 of FIG. 1.

In step 305, the through hole of the virtual positioning jig is defined at the implant region portion of the digital 3D representation. The through hole is defined such that it extends from the inner jig surface to the outer jig surface.

In step 306, the virtual positioning jig is finalized. Often no shelling is required in the case where a virtual bar structure is used, but there may be regions where material needs to be virtually added to ensure a sufficient thickness of the walls of the manufactured positioning jig or to add one or more features which improve the ease-of-handling of the positioning jig. There may also be regions where material needs to be virtually removed in order to avoid e.g. extensive use of material when manufacturing the positioning jig or to limit the production time.

As an alternative to the combined model approach the virtual dental restoration model and the digital 3D representation can be two independent units which are arranged relative to each other according to the target arrangement. The virtual bar structure can then be arranged in relation to the virtual dental restoration model and the digital 3D representation which then both are subtracted from the virtual bar structure to create the virtual positioning jig.

The virtual positioning jig is then created and can be used for manufacturing the positioning jig.

In step 307, the positioning jig is manufactured from the virtual positioning jig by direct digital manufacturing.

Figure 4:
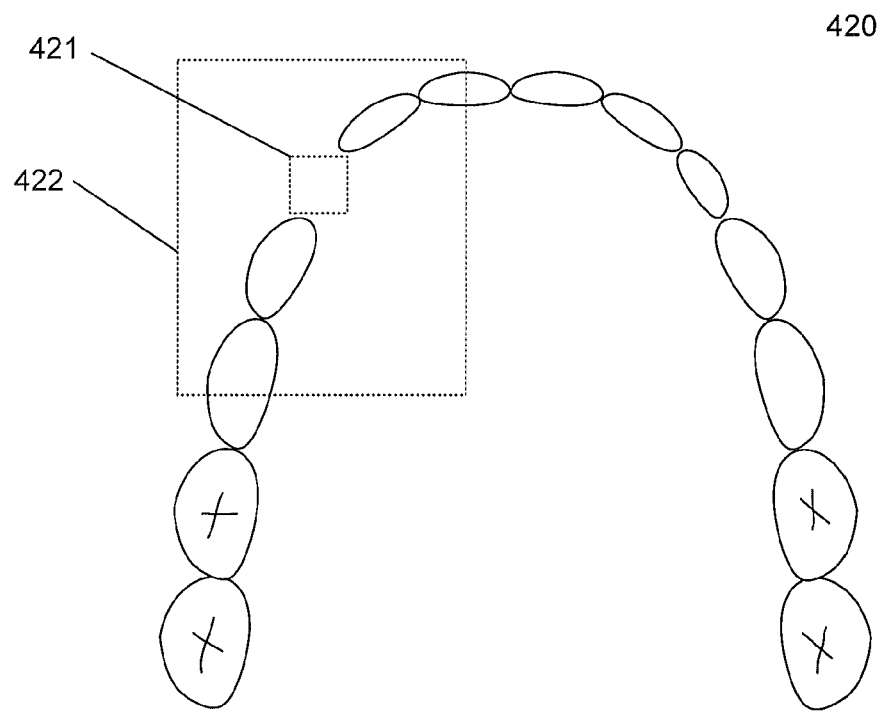
FIG. 4 shows a schematic of a patient's set of teeth.

FIG. 4 shows a schematic of a patient's set of teeth.

In this example the set of teeth is the maxillary teeth of the patient. The set of teeth 420 comprises the implant region 421 and a neighbor region 422. In the illustrated case, the neighbor region surrounds the implant region. In other situations the implant and neighbor regions may be arranged side by side, such that the manufactured positioning jig is to be arranged in relation to teeth on one side of the implant region.

A dental implant is secured or is to be secured in the patient's jaw-bone in the implant region, and the dental restoration is designed for being arranged at this implant secured to the implant using e.g. a retention screw.

Figure 5:
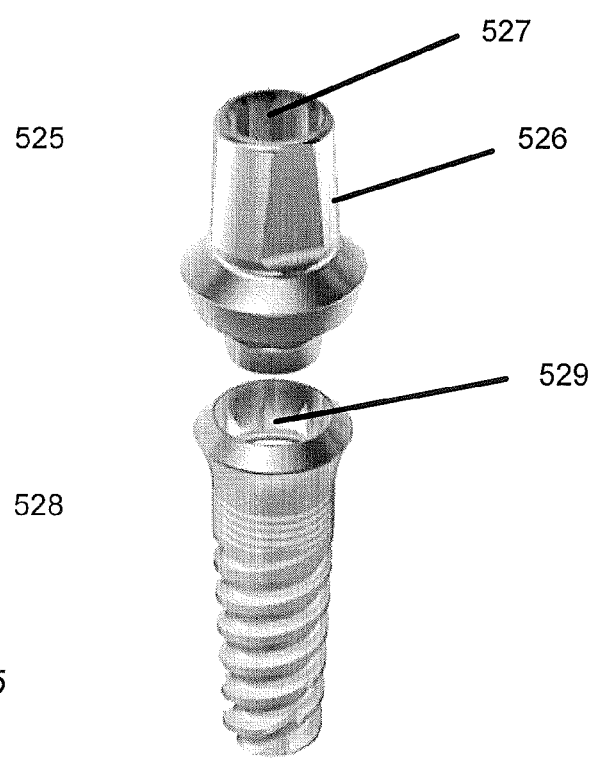
FIG. 5 shows a dental implant and a corresponding implant abutment.

FIG. 5 shows a dental implant and a corresponding implant abutment.

In this example, the dental restoration is an implant abutment 525. The dental implant 528 comprises an opening 529 to the screw thread cavity of the dental implant. The implant abutment 525 has an outer restoration surface 526 and a screw bore 527. The screw bore is adapted for allowing a retention screw to access the screw thread cavity of dental implant through the opening 529.

FIG. 6 shows a schematic of the combined virtual model.

Figure 6A:
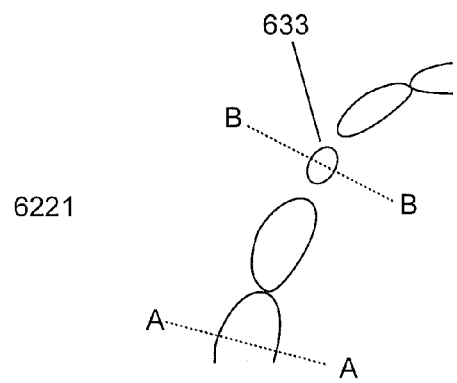
FIGS. 6A-6C show a schematic of the combined virtual model.

FIG. 6A shows a section 6221 of a combined virtual model obtained by combining the virtual dental restoration model 633 and the digital 3D representation of the set of teeth 620. In this example, the virtual dental restoration model is a virtual model of an implant abutment arranged according to its target arrangement in the combined virtual model. The section 6221 of the combined virtual model consists of the implant and neighbor region portions illustrated in FIG. 4.

Figure 6B:
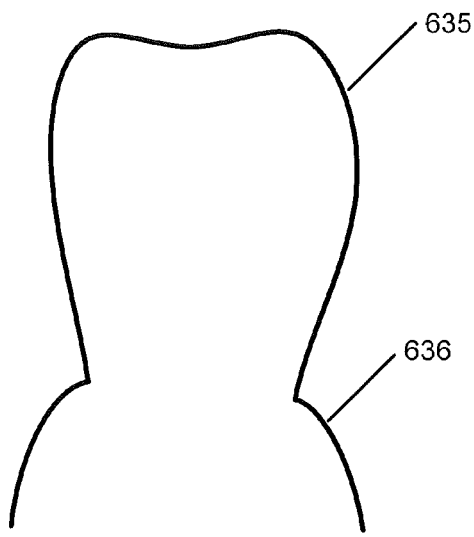

In FIG. 6B is shown the cross section of the combined virtual model in a plane which is defined by the line A-A indicated in FIG. 6A and a normal to the occlusal plane of the patient's teeth. The cross section shows the surface of a tooth 635 at the neighbor region portion of the combined virtual model and the gingiva 636 at this tooth.

Figure 6C:
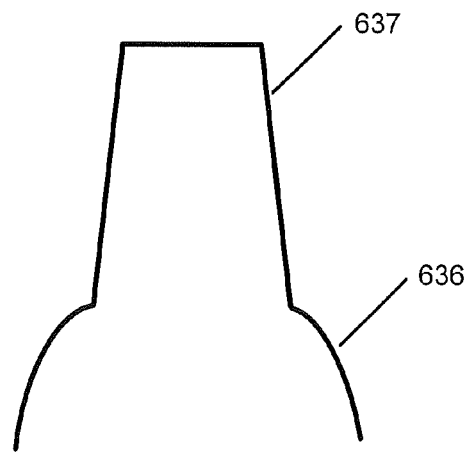

In FIG. 6C is shown the cross section of the combined virtual model a plane defined by the line B-B indicated in FIG. 6A and a normal to the occlusal plane of the patient's teeth. This line intersects the implant region portion of the combined virtual model and FIG. 6C shows a cross section of the outer restoration surface 637 and the gingiva 636 at the virtual model of the implant abutment.

FIG. 7 illustrates how the inner and outer jig surfaces can be generated using of a positioning jig 3D spline. The cross sections of the neighbor region portion and the implant region portion of the combined model are the same as illustrated in FIG. 6.

Figure 7A:
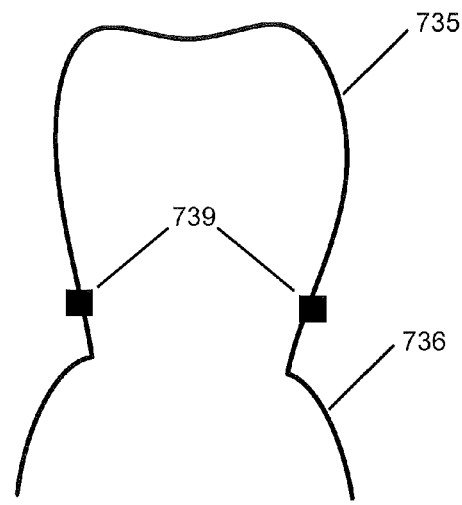
FIGS. 7A-7D illustrate how the inner and outer jig surfaces can be generated using a positioning jig 3D spline.

In FIG. 7A neighbor section 739 of the positioning jig 3D spline is defined in relation to the surface of a tooth 735 in the neighbor region portion of the combined virtual model.

Figure 7B:
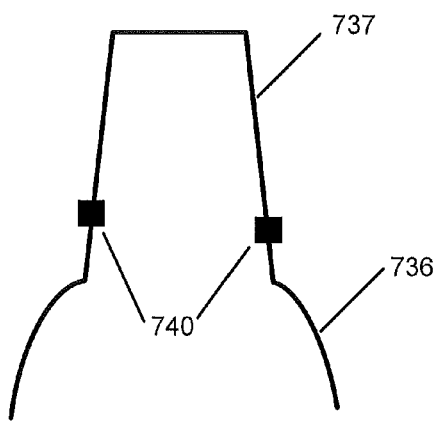

In FIG. 7B a dental restoration section 740 of the positioning jig 3D spline is defined in relation to the outer restoration surface 737, i.e. the outer surface of the virtual dental restoration model in the implant region portion of the combined virtual model.

The neighbor section 739 and the dental restoration section 740 are arranged above the gingiva at the tooth surface and at the outer restoration surface, respectively, such that the manufactured positioning jig will not contact the gingiva 736. This has the advantage that the discomfort of experiencing the positioning jig applying pressure on the gingiva is avoided.

Figure 7C:
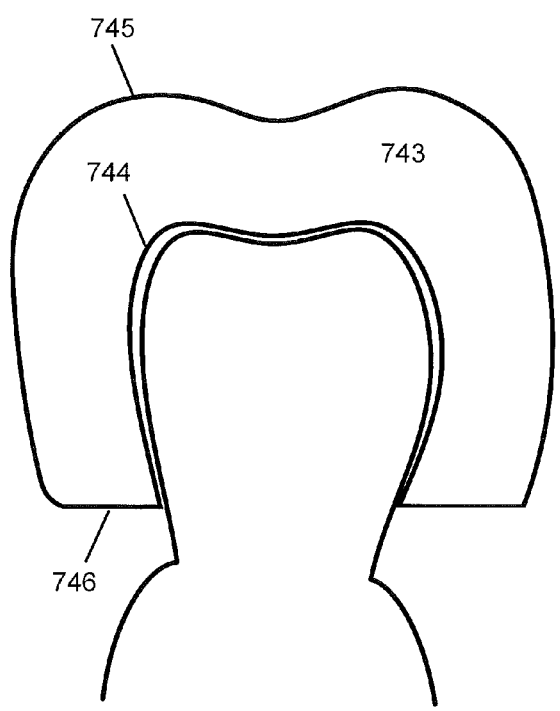
Figure 7D:
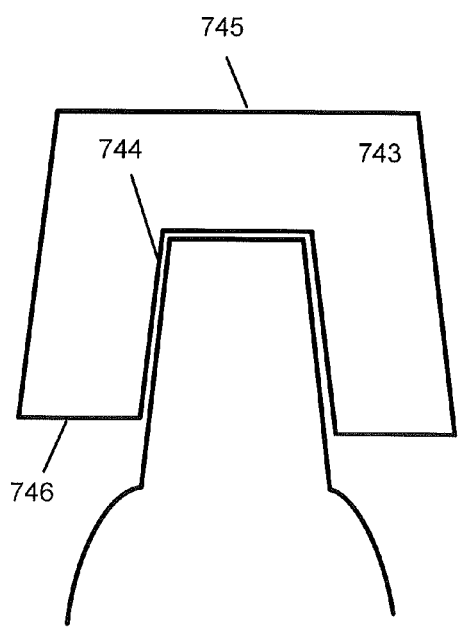

In FIG. 7C, the inner jig surface 744 is formed by copying the corresponding surface 735 of the combined virtual model. In the figure, a slight offset is provided to allow the inner jig surface to be distinguished from the combined virtual model. Equivalently, the inner jig surface 744 at the dental restoration model is formed in FIG. 7D by copying the outer restoration surface 737 of the combined virtual model. Here a slight offset is also provided to allow the inner jig surface to be distinguished from the combined virtual model.

The outer jig surface 745 is formed by a shelling of the inner jig surface 744. When finalizing the virtual positioning jig 743 the cervical facing portion 746 of the virtual positioning jig 743 is formed by a loofting process.

The position and shape of the cervical facing portion 746 along the arch of the set of teeth can be determined using said positioning jig 3D spline.

After the inner and outer jig surfaces are created, the through hole is defined at the appropriate position at the virtual restoration model.

FIG. 8 illustrates how the inner and outer jig surfaces can be generated using a virtual bar structure. The cross sections of the neighbor region portion and the implant region portion of the combined model are the same as illustrated in FIGS. 6 and 7. FIG. 8 further shows a cross sectional view of the virtual bar structure 850. The virtual bar structure 850 is configured for following the arch of the set of teeth in the implant region portion and the neighbor region portion of the digital 3D representation of the set of teeth.

FIG. 8A shows one arrangement of the virtual bar structure 850 in the neighbor region portion of the combined virtual model. The virtual bar structure 850 encloses part of the surface of a tooth 835 such that the occlusal surface and part of the lingual and buccal surfaces of the tooth 835 are covered by the virtual bar structure. Other configurations are also possible such as where only a part of the occlusal surface is covered in some sections of the virtual bar structure. FIG. 8B shows an arrangement of the virtual bar structure 850 in the implant region portion of the combined virtual model. The virtual bar structure 850 here encloses part of the outer restoration surface 837.

In both FIGS. 8A and 8B the virtual bar structure 850 is arranged such that the manufactured positioning jig will not contact the gingiva 836. This has the advantage that the discomfort of experiencing the positioning jig applying pressure on the gingiva is avoided.

The inner jig surface 844 and the outer jig surface 845 are then created by a Boolean subtraction of the combined virtual model from the virtual bar structure.

In FIG. 8C, the inner jig surface 844 at the neighbor region portion is formed by the Boolean subtraction of the corresponding surface 835 of the combined virtual model from the virtual bar structure 850. In the figure, a slight offset is provided to allow the inner jig surface to be distinguished from the combined virtual model.

Equivalently, the inner jig surface 844 at the dental restoration model in the implant region portion is formed by the Boolean subtraction of the corresponding surface of the combined virtual model from the virtual bar structure 850 as illustrated in FIG. 8D.

The outer jig surface 845 and the cervical facing portion 846 of the virtual positioning jig 843 are directly given by the outer surface of the virtual bar structure 850.

The position and shape of the cervical facing portion 846 along the arch of the set of teeth can be determined using said positioning jig 3D spline or can be determined directly from the shape of the virtual bar structure.

After the inner and outer jig surfaces are created, the through hole is defined at the appropriate position at the virtual restoration model.

FIG. 9 shows an example where the through hole is defined from an insertion volume.

Figure 9A:
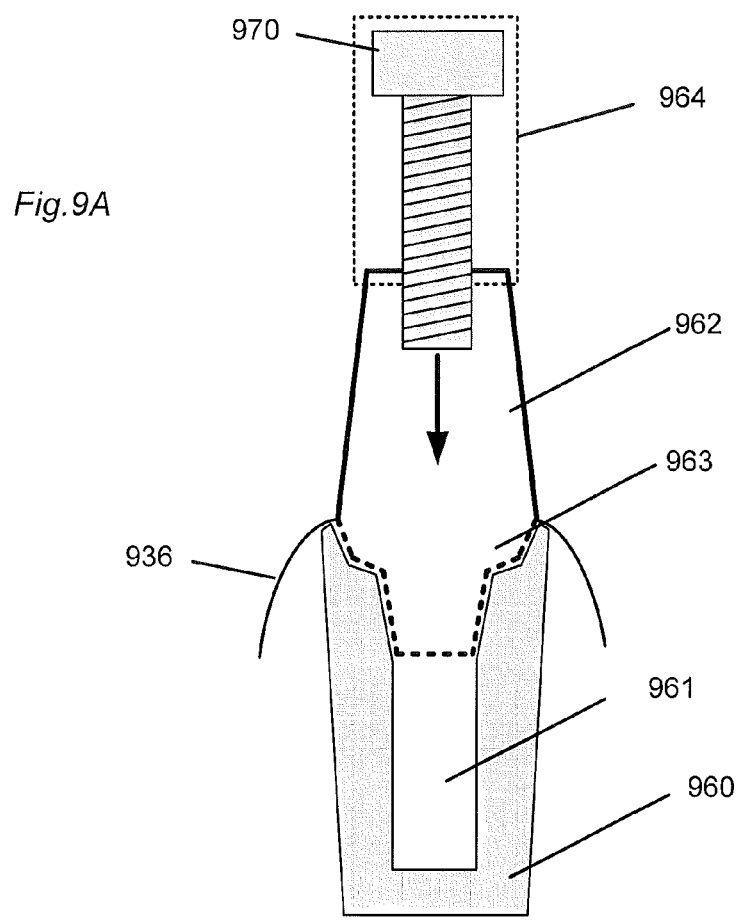
FIGS. 9A-9E show an example where the through hole is defined from an insertion volume.

A retention screw 970 is intended for securing a dental restoration at a dental implant 960 by engaging the screw cavity 961 of the dental implant. FIG. 9A shows an insertion volume 964 for the retention screw at the implant region portion of the digital 3D representation of the set of teeth. The insertion volume 964 is shaped according to a preferred insertion direction of the retention screw 970 and is sized to ensure that there is sufficient space to allow the retention screw to pass through the manufactured positioning jig to the dental restoration and the dental implant 960. The dental restoration is here an implant abutment with a visible part 962 (full line) above the gingiva and a sub-gingival part 963 (dotted line) arranged below the gingiva when the implant abutment is arranged at the dental implant.

Figure 9B:
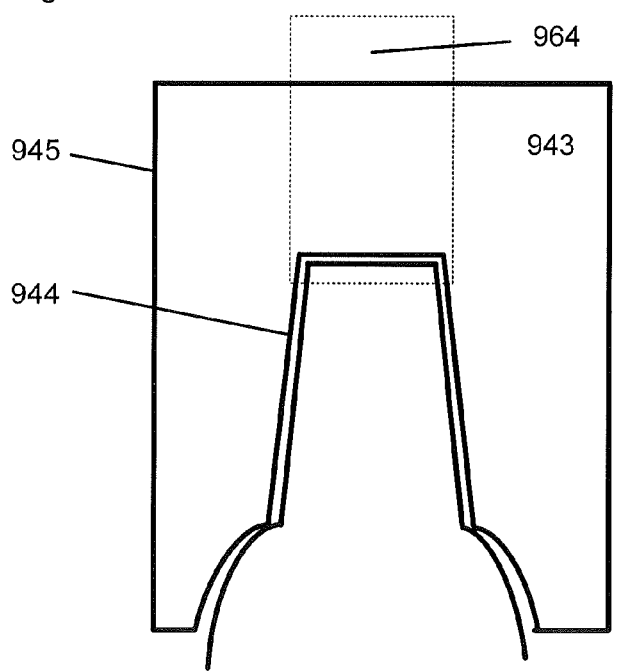

FIG. 9B shows an implant region cross section of a virtual positioning jig 943 with inner jig surface 944 and outer jig surface 945 corresponding to the A-A cross sectional plane discussed above, and with the insertion volume 964 visualized together with the virtual positioning jig 943. In this example, the virtual positioning jig 943 is created using a virtual bar structure as described in FIG. 8.

Figure 9C:
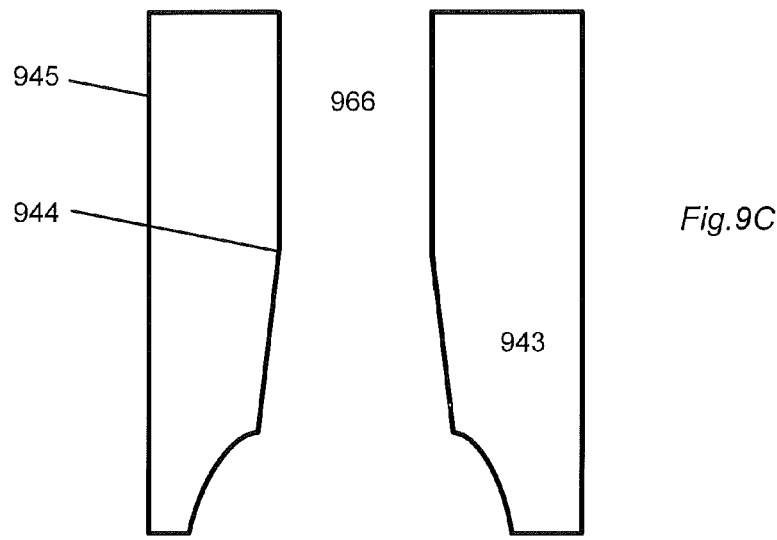

In FIG. 9C the insertion volume 964 is subtracted from the virtual positioning jig 943 such that a virtual through hole is formed providing a virtual passage to the implant region portion. For a manufactured positioning jig, the through hole provides a passage to the implant region, where the passage allows physical contact with the manufactured dental restoration arranged at the implant region through the positioning jig. At the neighbor region portion, the inner and outer jig surfaces of the virtual positioning jig are still defined by the virtual bar structure and have the shape illustrated in FIG. 8C.

Figure 9D:
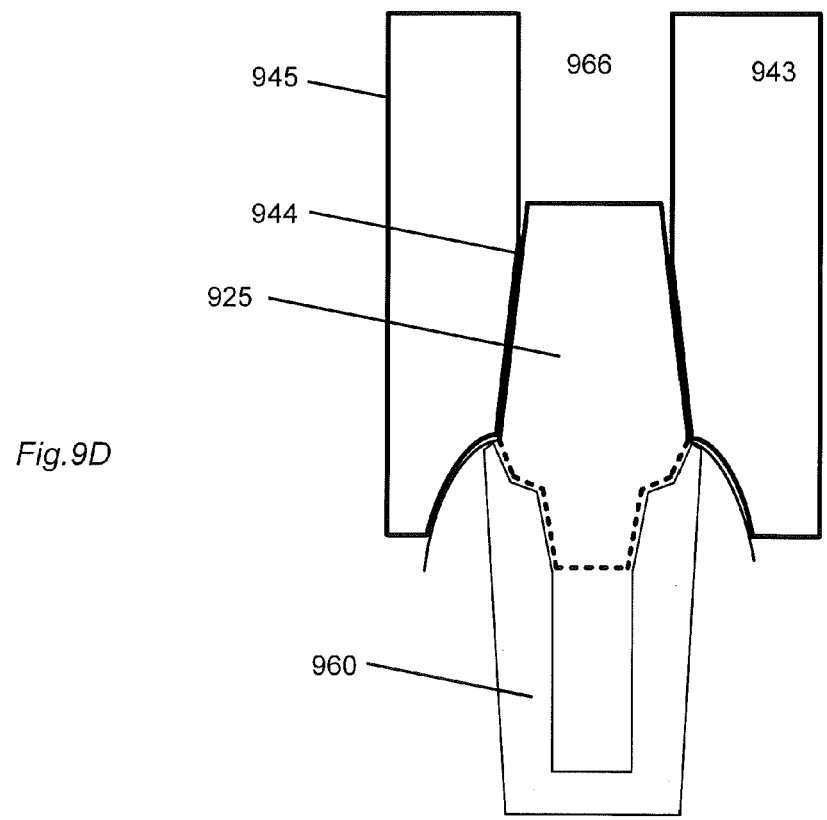

When the manufactured jig 943 is arranged in the patient's mouth, the through hole 966 allows the retention screw to access the screw thread cavity of the dental implant 960 as illustrated in FIG. 9D. When the dental restoration is secured at the implant, the manufactured positioning jig is applied to determine whether the dental restoration has the correct position and orientation relative to the patient's set of teeth. If this is the case, the manufactured positioning jig can be positioned such that it rests on the neighbor section of the patient's set of teeth while the outer surface of the dental restoration 925 is aligned with the inner surface 944 of the positioning jig.

Figure 9E:
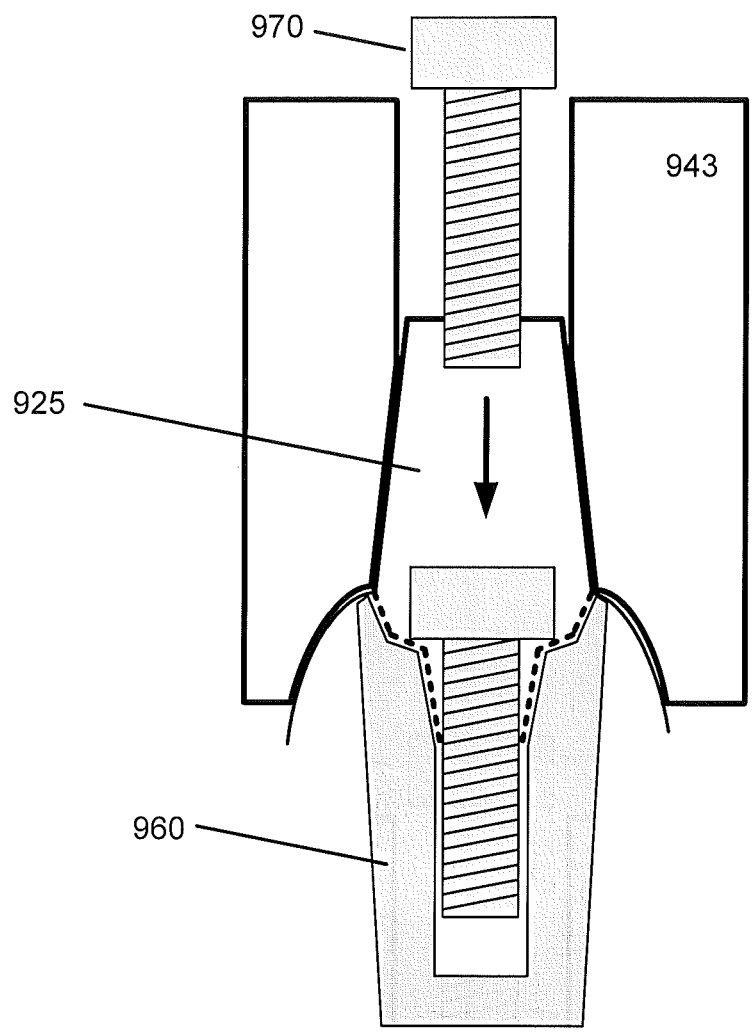

FIG. 9E illustrates how the retention screw 970 can be inserted along the arrow through the though hole of the positioning jig 943 and the dental restoration 925 to the screw cavity the dental implant 960 where it engages this cavity.

The disclosed method provides that the manufactured positioning jig has an inner surface which in the neighbor region is shaped according to the patient's teeth such that when it is placed on the teeth it is arranged in a well determined location relative to the teeth. In the implant region, the inner surface is shaped such that the manufactured dental restoration can only be arranged according to target arrangement and the through hole is located such that a retention screw can pass through the hole to the screw bore of the dental restoration.

Figure 10:
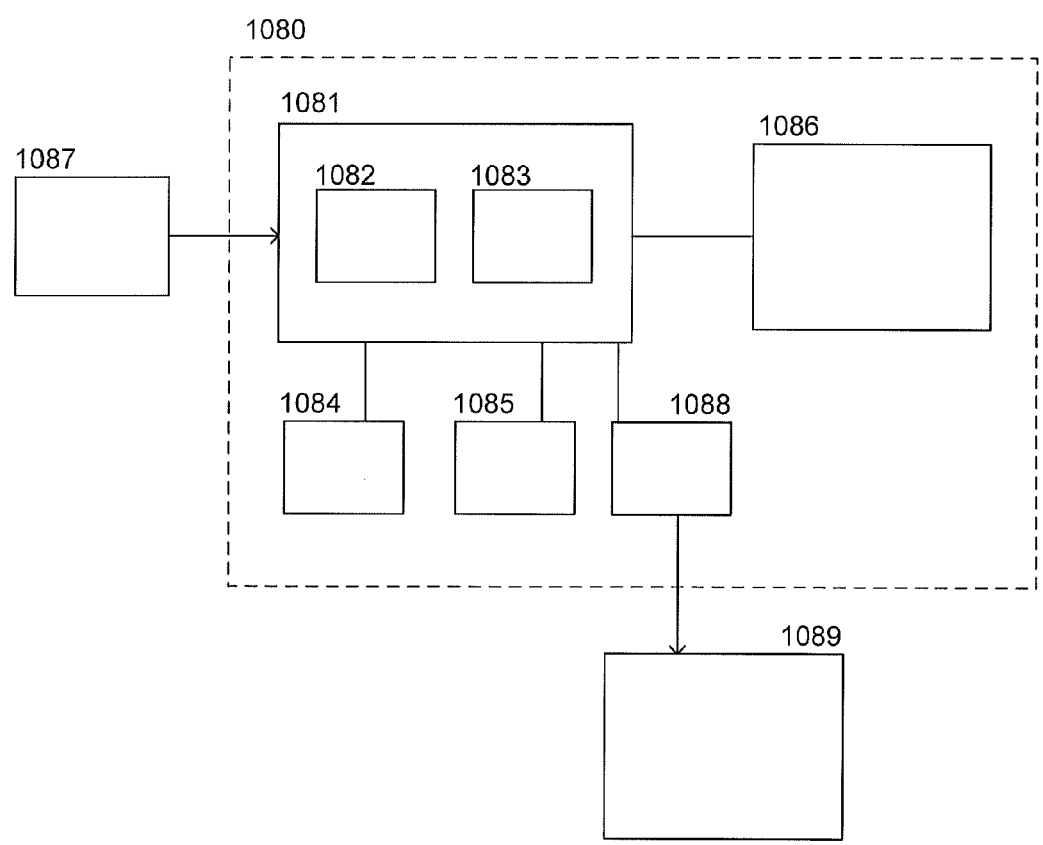
FIG. 10 shows a schematic of a system for implementing the method according to the present invention.

FIG. 10 shows a schematic of a system according to an embodiment of the present invention. The system 1080 comprises a computer device 1081 comprising a computer readable medium 1082 and a processor 1083. The system further comprises a visual display unit 1086, a computer keyboard 1084 and a computer mouse 1085 for entering data and activating virtual buttons visualized on the visual display unit 1086. The visual display unit 1086 can be a computer screen. The computer device 1081 is capable of receiving a digital 3D representation of the patient's set of teeth from a scanning device 1087, such as the TRIOS intra-oral scanner manufactured by 3shape NS, or capable of receiving scan data from such a scanning device and forming a digital 3D representation of the patient's set of teeth based on such scan data. The received or formed digital 3D representation can be stored in the computer readable medium 1082 and provided to the processor 1083. The processor 1083 is configured for designing a virtual model of the dental restoration at the digital 3D representation such that the designed virtual dental restoration model is arranged according to a target arrangement relative to the digital 3D representation, for creating an inner surface and an outer surface of the virtual positioning jig, where the inner jig surface is created based on said outer restoration surface, the target arrangement, and the neighbor region portion of the digital 3D representation; and for defining a through hole of the virtual positioning jig at the implant region portion of the digital 3D representation, where the through hole extends from the inner jig surface to the outer jig surface using the method according to any of the embodiments. In the designing, creating and defining of these features, one or more options can be presented to the operator, such as where the though hole is defined. Other options can relate to numerical values e.g. for the cross sectional diameter of the through hole. The options can be presented in a user interface visualized on the visual display unit 1086.

The system comprises a unit 1088 for transmitting the designed virtual 3D model to e.g. a computer aided manufacturing (CAM) device 1089 for manufacturing the positioning jig, the dental restoration and the drill guide, or to another computer system e.g. located at a milling center where these units can be manufactured. The unit for transmitting the virtual 3D model can be a wired or a wireless connection.

The scanning of the patient's set of teeth using the scanning device 1087 can be performed at a dentist while the designing of the virtual positioning jig, the dental restoration and the drill guide can be performed at a dental laboratory. In such cases the digital 3D representation of the patient's set of teeth can be provided via an internet connection between the dentist and the dental laboratory.

Figure 11:
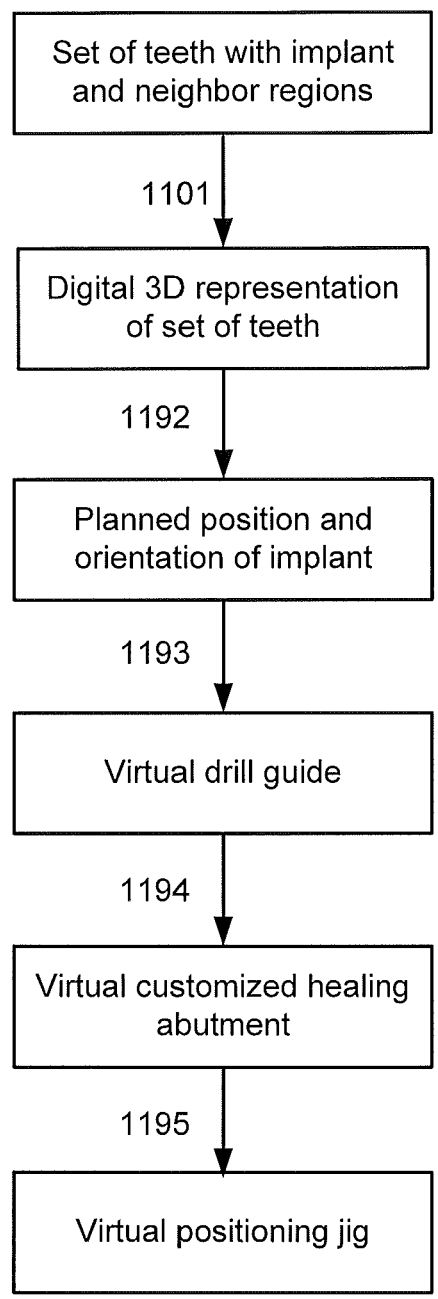
FIG. 11 shows a flow chart of a method for virtually creating a drill guide, a customized healing abutment and a positioning jig

FIG. 11 shows a flow chart of a method for virtually creating a drill guide, a customized healing abutment and a positioning jig from which virtual units a drill guide, a customized healing abutment and a positioning jig can be manufactured.

In step 1101, a digital 3D representation of the patient's set of teeth is obtained. For a computer-implemented method the digital 3D representation can be obtained by loading it into a data processing system on which the method is implemented. The digital 3D representation may be a result of a 3D scanning the set of teeth using e.g. an intra-oral scanner for direct 3D scanning of the teeth or by a 3D scanning of an impression or a physical model of the set of teeth.

The set of teeth comprises an implant region for or with a dental implant in which the manufactured dental restoration is to be secured using e.g. a retention screw. The set of teeth further comprises a neighbor region of the set of teeth which e.g. surrounds the implant region and/or is adjacent to the implant region. The 3D scanning of the set of teeth is such that the obtained digital 3D representation comprises an implant region portion relating to the implant region and a neighbor region portion relating to the neighbor region of the set of teeth.

In step 1192, the position and orientation of a dental implant in the patient's set of teeth is planned e.g. based on a CT scan of the patient showing the inferior alveolar nerve and the roots of the teeth in the neighbor region. In the acceptable position and orientation of the implant in the jaw bone there is no risk of contact with the nerve or teeth roots.

In step 1193, a virtual drill guide is created from which a drill guide can be manufactured. The drill guide is for guiding a dentist when surgically drilling a bore for the dental implant into the jaw bone at the implant region. The drill guide comprises a passage which guides the surgical drill such that when an implant is arranged in said drilled bore it is substantially arranged according to the planned position and orientation. The drill guide is preferable shaped to rest on the neighboring region of the patient's set of teeth.

In step 1194, the target arrangement of the virtual customized healing abutment relative to said digital 3D representation of the set of teeth is identified and a virtual model of the customized healing abutment is designed at the digital 3D representation such that it is arranged according to the target arrangement as also described in relation to FIG. 1. The customized healing abutment comprises a part configured for engaging the dental implant arranged in the drilled bore and a part that can form the gingiva of the implant region according to a preferred gingiva profile when the customized healing abutment is arranged according to the target arrangement;

In step 1195, the virtual positioning jig is created by creating the inner and outer surfaces of the virtual positioning jig and defining a through hole of the virtual positioning jig at the implant region portion of the digital 3D representation. The inner jig surface is created based on the outer surface of the customized healing abutment, the target arrangement, and the neighbor region portion of the digital 3D representation such that the manufactured positioning jig can confirm that the customized healing abutment is arranged according to the target arrangement. The through hole extends from the inner jig surface to the outer jig surface such that in the manufactured positioning jig the through hole provides access to the implant region through the positioning jig.

The portion of the inner jig surface which in the manufactured positioning jig is intended for contacting the dental restoration can be created by copying the part of the combined model corresponding to the dental restoration or by an offset of this part. The portion of the inner jig surface which in the manufactured positioning jig is intended for engaging the neighbor region of the set of teeth can be created by copying the corresponding part of the combined model such as by copying a part of the teeth and/or gingiva in this neighbor region portion of the digital 3D representation of the set of teeth.

The drill guide and the positioning jig may be designed based on the same surfaces of the neighbor section such that the difference between the drill guide and the positioning jig is the size and number of through holes and their shape in the implant region. In the positioning jig there is usually only one hole for each implant in which a dental restoration is to be arranged. In a drill guide there are often several additional though holes used for fixating the drill guide at the patient's set of teeth during the surgical drilling.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for creating a virtual positioning jig for manufacturing a positioning jig, where said manufactured positioning jig is configured for use when positioning a manufactured dental restoration at a patient's set of teeth, said method comprising:
   obtaining a digital 3D representation of the set of teeth, said digital 3D representation comprising an implant region portion relating to an implant region and a neighbor region portion relating to a neighbor region of the set of teeth;
   designing a virtual model of the dental restoration at the digital 3D representation such that the designed virtual dental restoration model is arranged according to a target arrangement relative to the digital 3D representation, said virtual dental restoration model comprising an outer restoration surface;
   creating an inner surface and an outer surface of the virtual positioning jig, where the inner jig surface is created based on said outer restoration surface, the target arrangement, and the neighbor region portion of the digital 3D representation; and
   defining a through hole of the virtual positioning jig at the implant region portion of the digital 3D representation, where the through hole extends from the inner jig surface to the outer jig surface.

2. The method according to claim 1, wherein the method comprises visualizing the virtual dental restoration model together with the digital 3D representation.

3. The method according to claim 1, wherein the method comprises combining the virtual dental restoration model and the digital 3D representation to obtain a combined virtual model.

4. The method according to claim 1, wherein the method comprises identifying the position and orientation of a dental implant in a jaw bone of the patient.

5. The method according to claim 4, where designing said virtual dental restoration model comprises defining a screw bore such that a dental restoration manufactured from the virtual dental restoration model can be attached to said dental implant using a retention screw configured for engaging said screw bore.

6. The method according to claim 4, wherein the target arrangement of said virtual dental restoration model relative to said digital 3D representation is determined from the identified position and orientation of the dental implant.

7. The method according to claim 4, wherein the arrangement of the through hole of the virtual positioning jig is determined based on the identified position and orientation of the dental implant.

8. The method according to claim 5, wherein a cross-sectional diameter of the through hole of the virtual positioning jig is determined from a known diameter of the retention screw and/or from a predetermined diameter.

9. The method according to claim 5, wherein the method comprises determining an insertion volume for the retention screw.

10. The method according to claim 9, wherein the insertion volume for the retention screw is determined from the identified position and orientation of the dental implant and/or from the designed virtual dental restoration model.

11. The method according to claim 9, wherein the through hole of the virtual positioning jig is defined by a Boolean subtraction of the insertion volume from the formed virtual body.

12. The method according to claim 1, wherein the method comprises generating a positioning jig 3D spline in relation to the digital 3D representation and/or in relation to the virtual dental restoration model and/or in relation to the combined virtual model.

13. The method according to claim 12, wherein at least part of a boundary of the inner jig surface is defined by the positioning jig 3D spline.

14. The method according to claim 12, wherein the positioning jig 3D spline comprises a neighbor section which is shaped according to the neighbor region portion of the digital 3D representation.

15. The method according to claim 12, wherein at least part of the neighbor section of the positioning jig 3D spline is shaped according to a line defined by an offset of a gingival margin of teeth in said neighbor region portion of the digital 3D representation.

16. The method according to claim 1, wherein the dental restoration comprises an implant abutment.

17. The method according to claim 16, wherein the positioning jig 3D spline is shaped according to a finish line of the implant abutment, or according to a line defined by an offset of said finish line.

18. The method according to claim 1, wherein the outer jig surface is created by a shelling of the inner jig surface.

19. The method according to claim 1, wherein creating the inner and the outer surface of the virtual positioning jig comprises defining a virtual bar structure in relation to the digital 3D representation and the virtual dental restoration model or in relation to the combined virtual model.

20. The method according to claim 1, wherein creating the inner jig surface and the outer jig surface comprises a Boolean subtraction of the digital 3D representation and the virtual dental restoration model from the virtual bar structure or a Boolean subtraction of the combined virtual model from the virtual bar structure.

21. The method according to claim 1, wherein a diagnostic wax-up for the set of teeth is created and where the inner jig surface is created based on said diagnostic wax-up.

* * * * *